United States Patent
Tomura et al.

(10) Patent No.: US 6,901,785 B2
(45) Date of Patent: Jun. 7, 2005

(54) GAS CONCENTRATION MEASURING APPARATUS DESIGNED TO MINIMIZE MEASUREMENT ERROR

(75) Inventors: Takanao Tomura, Nishio (JP); Michiyasu Moritsugu, Okazaki (JP); Eiichi Kurokawa, Okazaki (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 49 days.

(21) Appl. No.: 10/327,942

(22) Filed: Dec. 26, 2002

(65) Prior Publication Data

US 2003/0121310 A1 Jul. 3, 2003

(30) Foreign Application Priority Data

Dec. 27, 2001 (JP) .......................................... 2001-397348
Nov. 5, 2002 (JP) .......................................... 2002-321043

(51) Int. Cl.[7] .......................................... G01N 27/419
(52) U.S. Cl. ..................... 73/31.05; 73/23.31; 204/425; 204/426; 204/427
(58) Field of Search ............................. 73/23.31, 31.05; 204/424–427, 431, 435

(56) References Cited

U.S. PATENT DOCUMENTS

| 5,866,799 A | 2/1999 | Kato et al. .................. 73/31.05 |
| 6,295,862 B1 | 10/2001 | Kurokawa et al. ......... 73/31.05 |

FOREIGN PATENT DOCUMENTS

| EP | 0798555 A2 | 10/1997 |
| JP | 9-318596 | 12/1997 |
| JP | 2885336 | 2/1999 |
| JP | 2000-137018 | 5/2000 |

*Primary Examiner*—Daniel S. Larkin
(74) *Attorney, Agent, or Firm*—Nixon & Vanderhye P.C.

(57) ABSTRACT

A gas concentration measuring apparatus has a gas sensor consisting of pump, sensor, and monitor cells. The apparatus works to determine the value of voltage applied to the pump cell when a change in current produced by the monitor cell or the sensor cell changes upon a change in the voltage applied to the pump cell varies greatly and uses it to determine a control point to which the voltage applied to the pump cell is to be controlled. This keeps a gas concentration measuring accuracy free from, for example, aging of the sensor.

24 Claims, 23 Drawing Sheets

SHIFT IN INFLECTION POINT

SHIFT IN INFLECTION POINT

GAS CONCENTRATION MEASURING APPARATUS DESIGNED TO MINIMIZE MEASUREMENT ERROR

BACKGROUND OF THE INVENTION

1. Technical Field of the Invention

The present invention relates generally to a gas concentration measuring apparatus for measuring the concentration of a given gas which may be employed in an air-fuel ratio control system for automotive vehicles, and more particularly to a such a gas concentration measuring apparatus designed to minimize an error in determining the concentration of a gas.

2. Background Art

Limiting current type gas concentration sensors are known which are used for measuring NOx contained in exhaust gasses of an automotive engine. There is used one of such gas concentration sensors which includes a pump cell and a sensor cell which are made of solid electrolyte bodies. The pump cell works to pump oxygen ($O_2$) contained in gasses admitted into a gas chamber out of the sensor and to pump oxygen ($O_2$) of outside gasses into the gas chamber selectively. The sensor cell works to measure the concentration of NOx contained in the gasses after passing through the pump cell. The pump cell and the sensor cell are designed to produce current signals indicative of the concentration of oxygen and NOx upon application of voltage thereto.

Another type of gas concentration sensor is known which includes a monitor cell in addition to the pump cell and the sensor cell. The monitor cell works to produce an electromotive force as a function of the concentration of oxygen within the gas chamber. A control system is also proposed which controls the voltage to be applied to the pump cell of such a three-cell gas concentration sensor as a function of a difference between an actual value and a target value of the electromotive force of the monitor cell.

For example, Japanese Patent No. 2885336 discloses the above type of gas concentration sensor.

The above discussed gas concentration sensors, however, have the drawback in that a unit-to-unit difference and/or aging of the sensors usually results in a change in resistance or impedance of a solid electrolyte body, thereby leading to a decrease in accuracy of determining the concentration of a gas.

SUMMARY OF THE INVENTION

It is therefore a principal object of the present invention to avoid the disadvantages of the prior art.

It is another object of the present invention to provide a gas concentration measuring apparatus designed to eliminate an error in determining the concentration of a specified gas component of measurement gases arising from a unit-to-unit difference and/or aging of a gas concentration sensor.

According to one aspect of the invention, there is provided a gas concentration measuring apparatus which may be employed with an automotive control system designed to control the quantity of fuel injected into an internal combustion gasoline engine as a function of an output of the gas concentration measuring apparatus under feedback (F/B) control to bring the air-fuel (A/F) ratio into agreement with a target value. The gas concentration measuring apparatus comprises: (a) a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current as a function of a concentration of a specified gas component contained in the gasses having passed through the pump cell, and a monitor cell working to produce a monitor cell current indicative of a concentration of residual oxygen molecules within the gas chamber, the monitor cell having a given pump cell applied voltage-to-monitor cell current characteristic in which the monitor cell current changes as a function of a pump cell-applied voltage applied to the pump cell; and (b) a controller working to determine a value of the pump cell-applied voltage when a value of the monitor cell current changes greatly at a given rate in the pump cell applied voltage-to-monitor cell current characteristic. The controller also determines a control point to which the voltage applied to the pump cell is to be controlled using the value of the pump cell-applied voltage.

The voltage applied to the pump cell (which will also be labeled Vp below) and the monitor cell current (which will also be labeled Im below) have a relation in which the monitor cell current Im changes at a greater rate within a range of lower levels of the pump cell-applied voltage and remains unchanged substantially within a range of higher levels of the pump cell-applied voltage (see a Vp-Im curve in FIG. 2(b)). Specifically, the pump cell applied voltage-to-monitor cell current relation or characteristic has an inflection point at which the rate of a change in monitor cell current Im changes greatly. The relation between the pump cell-applied voltage and the sensor cell current (which will also be labeled Is below) has a flat range in which the sensor cell current Is hardly changes regardless of a change in the pump cell-applied voltage. Within the flat range, it is possible to measure the concentration of a gas component such as NOx contained in exhaust gasses of automotive engines accurately (see a Vp-Is curve in FIG. 2(b)). The inflection point of the monitor cell current lies within or slightly outside the flat range of the sensor cell current. The locational relation between the inflection point of the monitor cell current and the flat range of the sensor cell current is usually constant in each type of gas concentration sensor. In other words, a correlation between the inflection point of the monitor cell current and the flat range of the sensor cell current is usually constant free from a change in resistance of the gas concentration sensor resulting from aging and a unit-to-unit difference of the gas concentration sensor. Production of the sensor cell current within the flat range may, therefore, be accomplished by determining the value of the pump cell-applied voltage provided at the inflection point of the monitor cell in the pump cell applied voltage-to-monitor cell current characteristic and using it to correct the voltage to be applied to the pump cell, thereby keeping the accuracy of measuring the concentration of the gas free from the unit-to-unit difference and/or aging of the gas concentration sensor.

The value of the pump cell-applied voltage provided at the inflection point of the monitor cell current in the pump cell applied voltage-to-monitor cell current characteristic, as referred to herein, is the value of the voltage applied to the pump cell when changed, for example, from a higher to a lower voltage side, and the rate of a resulting change in the monitor cell current varies greatly. For instance, it is defined by the voltage applied to the pump cell when changed in a unit of 2 mV to 10 mV, and a resulting change in the monitor cell current has increased 1.2 times.

In the preferred mode of the invention, as described above, the controller changes the voltage applied to the pump cell stepwise cyclically at given amplitudes to one of higher and lower voltage sides and measures a resulting value of the monitor cell current to determine the value of the pump cell-applied voltage when the value of the monitor cell current changes greatly in the pump cell applied voltage-to-monitor cell current characteristic.

The gas concentration measuring apparatus may further comprise a pump cell-applied voltage determining circuit which looks up a predetermined voltage-to-current relation and determines an initial value of the voltage to be applied to the pump cell as a function of an instant value of the pump cell current produced by the pump cell. The controller changes the initial value stepwise cyclically to the one of higher and lower voltage sides and measures the resulting value of the monitor cell current to determine the value of the pump cell-applied voltage when the value of the monitor cell current changes greatly in the pump cell applied voltage-to-monitor cell current characteristic.

The given amplitudes at which the voltage applied to the pump cell are changed may be constant or alternatively decreased in sequence.

The controller may determine the value of the pump cell-applied voltage when the value of the monitor cell current changes greatly as the control point.

The controller may add a given offset value to the value of the pump cell-applied voltage when the value of the monitor cell current changes greatly and define it as the control point. The offset value is a difference between a value of the pump cell-applied voltage causing the sensor cell current to be produced in a flat range within which the sensor cell current is kept substantially constant and the value of the pump cell-applied voltage when the value of the monitor cell current changes greatly determined by the controller. The difference is predetermined depending upon a type of the gas concentration sensor.

The controller may change the voltage applied to the pump cell to determine a fist pump cell-applied voltage at which the value of the monitor cell current changes greatly and further change the voltage applied to the pump cell to determine a second pump cell-applied voltage at which the monitor cell current becomes constant in level. The controller may define the second pump cell voltage as the control point of the voltage to be applied to the pump cell. For instance, the controller changes the voltage applied to the pump cell stepwise cyclically at given amplitudes in a first voltage level direction to determine the first pump cell-applied voltage and then changes the voltage applied to the pump cell stepwise cyclically at given amplitudes in a second voltage level direction opposite the first voltage level direction to determine the second pump cell-applied voltage. The amplitudes at which the voltage applied to the pump cell is changed to determine the first pump cell-applied voltage may be set greater than those at which the voltage applied to the pump cell is changed to determine the second pump cell-applied voltage, thereby resulting in a decreased time required for finding the first pump cell-applied voltage (i.e., the inflection point of the monitor cell current) and increased accuracy of finding the second pump cell-applied voltage (i.e., the control point).

The controller may compare between values of the monitor cell current produced before and after the voltage applied to the pump cell is changed in each cycle to determine the value of the pump cell-applied voltage when the value of the monitor cell current changes greatly.

The controller may define a value of the monitor cell current corresponding to an initial value of the voltage applied to the pump cell as a reference value and measure a change in the monitor cell current from the reference value in each cycle for use in determining the value of the value of the pump cell-applied voltage when the value of the monitor cell current changes greatly. This minimizes an adverse effect of a noise contained in the monitor cell current.

The controller may define a value of the monitor cell current produced outside a flat range within which the monitor cell current is kept substantially constant as a reference value and measure a change in the monitor cell current from the reference value in each cycle for use in determining the value of the value of the pump cell-applied voltage when the value of the monitor cell current changes greatly. This also minimizes the adverse effect of the noise contained in the monitor cell current and eliminates an undesirable change in the monitor cell current within the flat range in determining the value of the value of the pump cell-applied voltage when the value of the monitor cell current changes greatly.

The controller may sweep the voltage applied to the pump cell to one of the higher and lower voltage sides in each cycle in which the voltage is changed stepwise and monitor a resulting waveform of the monitor cell current to determine the value of the pump cell-applied voltage when the value of the monitor cell current changes greatly. This eliminates the need for waiting convergence of a change in the monitor cell current when the voltage is swept for determining the value of the value of the pump cell-applied voltage when the value of the monitor cell current changes greatly.

The controller may sweep the voltage applied to the pump cell to at least one of the higher and lower voltage sides when starting to determine the value of the pump cell-applied voltage when the value of the monitor cell current changes greatly and measure a resultant waveform of the monitor cell current to determine whether the voltage to be applied to the pump cell should be controlled or not. The aging and/or unit-to-unit difference of the gas concentration sensor may results in a shift in the pump cell applied voltage-to-monitor cell current characteristic. Such a shift may be found correctly by sweeping the voltage applied to the pump cell temporarily, which enables the voltage applied to the pump cell to be controlled only as needed.

The controller may sweep the voltage applied to the pump cell to at least one of the higher and lower voltage sides and monitor a resultant waveform of the monitor cell current to determine the value of the pump cell-applied voltage when the value of the monitor cell current changes greatly.

The controller may also sweep the voltage applied to the pump cell cyclically at different amplitudes and monitor the resultant waveform of the monitor cell current in each cycle to determine the value of the pump cell-applied voltage when the value of the monitor cell current changes greatly. This improves the accuracy of finding the value of the pump cell-applied voltage when the value of the monitor cell current changes greatly.

The controller may sweep the voltage being applied to the pump cell sequentially both to the higher and lower voltage sides and measure resulting changes in the monitor cell current. When the resulting changes are substantially identical with each other, the controller determines that the value of the pump cell-applied voltage when the value of the monitor cell current changes greatly remains unchanged. When the value of the voltage applied to the pump cell is provided within the flat range of the monitor cell current and away from the inflection point thereof, the changes in the monitor cell current are substantially equal to each other. If this is one of original characteristics of the gas concentration sensor, the controller may decide that the inflection point of the monitor cell remains unchanged. Therefore, if the changes in the monitor cell currents are different from each other, the controller may decide that the inflection point of the monitor cell has been shifted.

The controller may sweep the value of the voltage being applied to the pump cell both to the higher and lower voltage sides sequentially to measure the resulting changes in the monitor cell current, respectively. When the changes are different from those appearing at an initial characteristic of the gas concentration sensor and from each other, the controller determines that the value of the pump cell-applied voltage when the value of the monitor cell current changes greatly has shifted in a direction opposite a direction in which a change in the voltage applied to the pump cell results in an increase in the monitor cell current.

The controller may control the voltage applied to the pump cell as a function of the pump cell current produced by the pump cell by look-up using a predetermined voltage-to-current relation and determine the concentration of the specified gas component in a gas concentration measuring cycle. The controller may work to determine the control point and correct the voltage applied to the pump cell to the control point in a correction cycle which does not coincide with the gas concentration measuring cycle.

The aging of the gas concentration sensor will result in an increase in resistance (i.e., an impedance) thereof. This causes the quantity of oxygen remaining within the gas chamber to be changed even under control of the voltage applied to the pump cell. Practically, the quantity of oxygen pumped out of the gas chamber is insufficient, thus resulting in an increase in oxygen remaining within the gas chamber. Thus, it is advisable that the gas concentration measuring apparatus further comprise a deterioration determining circuit which works to determine a degree of deterioration of the gas concentration sensor based on the value of the pump cell-applied voltage when the value of the monitor cell current changes greatly.

The controller may look up a predetermined voltage-to-current relation to determine the value of the voltage to be applied to the pump cell as a function of an instant value of the pump cell current produced by the pump cell. The controller may define a difference between a value of the pump cell-applied voltage on the control point and the value of the voltage applied to the pump cell determined using the voltage-to-current relation as a voltage correction value and store the voltage correction value in a backup memory.

The controller may correct the voltage-to-current relation using a value of the pump cell-applied voltage on the control point.

The gasses admitted into the gas chamber may be exhaust gasses of an automotive engine. The controller may work to control the voltage to be applied to the pump cell at startup or rest of the engine.

According to the second aspect of the invention, there is provided a gas concentration measuring apparatus which comprises: (a) a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current indicating a concentration of a specified gas component contained in the gasses having passed through the pump cell, and a monitor cell working to produce a monitor cell current indicative of a concentration of residual oxygen molecules within the gas chamber, the monitor cell having a given pump cell applied voltage-to-monitor cell current characteristic in which the monitor cell current changes as a function of a pump cell-applied voltage applied to the pump cell; (b) a first circuit working to determine a value of the pump cell-applied voltage when a value of the monitor cell current changes greatly at a given rate in the pump cell applied voltage-to-monitor cell current characteristic; and (c) a second circuit which works to determine a degree of deterioration of the gas concentration sensor based on the value of the pump cell-applied voltage when the value of the monitor cell current changes greatly.

In the preferred mode of the invention, the second circuit determines that the degree of deterioration has increased as the value of the pump cell-applied voltage when the value of the monitor cell current changes greatly is shifted to the higher voltage side.

The gasses admitted into the gas chamber may be exhaust gasses of an automotive engine. The second circuit may work to determine the degree of deterioration at startup or rest of the engine.

According to the third aspect of the invention, there is provided a gas concentration measuring apparatus which comprises: (a) a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current as a function of a concentration of a specified gas component contained in the gasses having passed through the pump cell, and a monitor cell working to produce a monitor cell current indicative of a concentration of residual oxygen molecules within the gas chamber, the sensor cell having a given pump cell applied voltage-to-sensor cell current characteristic in which the sensor cell current changes as a function of a pump cell-applied voltage applied to the pump cell; and (b) a controller working to determine a value of the pump cell-applied voltage when a value of the sensor cell current changes greatly at a given rate in the pump cell applied voltage-to-sensor cell current characteristic. The controller also determines a control point to which the voltage applied to the pump cell is to be controlled using the value of the pump cell-applied voltage.

The voltage applied to the pump cell and the sensor cell current have a relation in which the sensor cell current Im changes at a greater rate within a range of lower levels of the pump cell-applied voltage and remains unchanged substantially within a range of higher levels of the pump cell-applied voltage (see a Vp-Is curve in FIG. 2($b$)). Specifically, the pump cell applied voltage-to-sensor cell current relation or characteristic has an inflection point at which the rate of a change in sensor cell current Is changes greatly. The locational relation between the inflection point of the sensor cell current and the flat range of the sensor cell current is constant in each type of gas concentration sensor. Therefore, the controller, as described above, may determine the control point to which the voltage applied to the pump cell is to be controlled using the value of the pump cell-applied voltage when the value of the sensor cell current changes greatly. This keeps the accuracy of measuring the concentration of the gas free from the unit-to-unit difference and/or aging of the gas concentration sensor.

The value of the pump cell-applied voltage provided at the inflection point of the sensor cell current in the pump cell applied voltage-to-sensor cell current characteristic, as referred to herein, is the value of the voltage applied to the pump cell when changed, for example, from a higher to a lower voltage side, and the rate of a resulting change in the sensor cell current varies greatly. For instance, it is defined by the voltage applied to the pump cell when changed in a unit of 2 mV to 10 mV, and a resulting change in the sensor cell current has increased 1.2 times.

In the preferred mode of the invention, as described above, the controller changes the voltage applied to the pump cell stepwise cyclically at given amplitudes to one of higher and lower voltage sides and measures a resulting value of the sensor cell current to determine the value of the pump cell-applied voltage when the value of the sensor cell current changes greatly in the pump cell applied voltage-to-sensor cell current characteristic.

The gas concentration measuring apparatus may further comprise a pump cell-applied voltage determining circuit which looks up a predetermined voltage-to-current relation and determines an initial value of the voltage to be applied to the pump cell as a function of an instant value of the pump cell current produced by the pump cell. The controller changes the initial value stepwise cyclically to the one of higher and lower voltage sides and measures the resulting value of the sensor cell current to determine the value of the pump cell-applied voltage when the value of the sensor cell current changes greatly in the pump cell applied voltage-to-sensor cell current characteristic.

The given amplitudes at which the voltage applied to the pump cell are changed may be constant or alternatively decreased in sequence.

The controller may determine the value of the pump cell-applied voltage when the value of the sensor cell current changes greatly as the control point.

The controller may add a given offset value to the value of the pump cell-applied voltage when the value of the sensor cell current changes greatly and define it as the control point.

The controller may change the voltage applied to the pump cell to determine a fist pump cell-applied voltage at which the value of the sensor cell current changes greatly and further change the voltage applied to the pump cell to determine a second pump cell-applied voltage at which the sensor cell current becomes constant in level. The controller may define the second pump cell voltage as the control point of the voltage to be applied to the pump cell. For instance, the controller changes the voltage applied to the pump cell stepwise cyclically at given amplitudes in a first voltage level direction to determine the first pump cell-applied voltage and then changes the voltage applied to the pump cell stepwise cyclically at given amplitudes in a second voltage level direction opposite the first voltage level direction to determine the second pump cell-applied voltage. The amplitudes at which the voltage applied to the pump cell is changed to determine the first pump cell-applied voltage may be set greater than those at which the voltage applied to the pump cell is changed to determine the second pump cell-applied voltage, thereby resulting in a decreased time required for finding the first pump cell-applied voltage (i.e., the inflection point of the sensor cell current) and increased accuracy of finding the second pump cell-applied voltage (i.e., the control point).

The controller may compare between values of the sensor cell current produced before and after the voltage applied to the pump cell is changed in each cycle to determine the value of the pump cell-applied voltage when the value of the sensor cell current changes greatly.

The controller may define a value of the sensor cell current corresponding to an initial value of the voltage applied to the pump cell as a reference value and measure a change in the sensor cell current from the reference value in each cycle for use in determining the value of the value of the pump cell-applied voltage when the value of the sensor cell current changes greatly. This minimizes an adverse effect of a noise contained in the sensor cell current.

The controller may define a value of the sensor cell current produced outside a flat range within which the sensor cell current is kept substantially constant as a reference value and measure a change in the sensor cell current from the reference value in each cycle for use in determining the value of the value of the pump cell-applied voltage when the value of the sensor cell current changes greatly. This also minimizes the adverse effect of the noise contained in the sensor cell current and eliminates an undesirable change in the sensor cell current within the flat range in determining the value of the value of the pump cell-applied voltage when the value of the sensor cell current changes greatly.

The controller may sweep the voltage applied to the pump cell to one of the higher and lower voltage sides in each cycle in which the voltage is changed stepwise and monitor a resulting waveform of the sensor cell current to determine the value of the pump cell-applied voltage when the value of the sensor cell current changes greatly. This eliminates the need for waiting convergence of a change in the sensor cell current when the voltage is swept for determining the value of the value of the pump cell-applied voltage when the value of the sensor cell current changes greatly.

The controller may sweep the voltage applied to the pump cell to at least one of the higher and lower voltage sides when starting to determine the value of the pump cell-applied voltage when the value of the sensor cell current changes greatly and measure a resultant waveform of the sensor cell current to determine whether the voltage to be applied to the pump cell should be controlled or not. The aging and/or unit-to-unit difference of the gas concentration sensor may results in a shift in the pump cell applied voltage-to-sensor cell current characteristic. Such a shift may be found correctly by sweeping the voltage applied to the pump cell temporarily, which enables the voltage applied to the pump cell to be controlled only as needed.

The controller may sweep the voltage applied to the pump cell to at least one of the higher and lower voltage sides and monitor a resultant waveform of the sensor cell current to determine the value of the pump cell-applied voltage when the value of the sensor cell current changes greatly.

The controller may also sweep the voltage applied to the pump cell cyclically at different amplitudes and monitor the resultant waveform of the sensor cell current in each cycle to determine the value of the pump cell-applied voltage when the value of the sensor cell current changes greatly. This improves the accuracy of finding the value of the pump cell-applied voltage when the value of the sensor cell current changes greatly.

The controller may sweep the voltage being applied to the pump cell sequentially both to the higher and lower voltage sides and measure resulting changes in the sensor cell current. When the resulting changes are substantially identical with each other, the controller determines that the value of the pump cell-applied voltage when the value of the sensor cell current changes greatly remains unchanged. When the value of the voltage applied to the pump cell is provided within the flat range of the sensor cell current and away from the inflection point thereof, the changes in the sensor cell current are substantially equal to each other. If this is one of original characteristics of the gas concentration sensor, the controller may decide that the inflection point of the sensor cell remains unchanged. Therefore, if the changes in the sensor cell currents are different from each other, the controller may decide that the inflection point of the sensor cell has been shifted.

The controller may control the voltage applied to the pump cell as a function of the pump cell current produced by the pump cell by look-up using a predetermined voltage-to-current relation and determine the concentration of the specified gas component in a gas concentration measuring cycle. The controller may work to determine the control point and correct the voltage applied to the pump cell to the control point in a correction cycle which does not coincide with the gas concentration measuring cycle.

The controller may control the voltage applied to the pump cell as a function of the pump cell current produced by the pump cell by look-up using a predetermined voltage-to-current relation and determine the concentration of the specified gas component in a gas concentration measuring cycle. The controller may work to determine the control point and correct the voltage applied to the pump cell to the control point in a correction cycle which uncoincides with the gas concentration measuring cycle.

The aging of the gas concentration sensor will result in an increase in resistance (i.e., an impedance) thereof. This causes the quantity of oxygen remaining within the gas chamber to be changed even under control of the voltage applied to the pump cell. Practically, the quantity of oxygen pumped out of the gas chamber is insufficient, thus resulting in an increase in oxygen remaining within the gas chamber. Thus, it is advisable that the gas concentration measuring apparatus further comprise a deterioration determining circuit which works to determine a degree of deterioration of the gas concentration sensor based on the value of the pump cell-applied voltage when the value of the sensor cell current changes greatly.

The controller may look up a predetermined voltage-to-current relation to determine the value of the voltage to be applied to the pump cell as a function of an instant value of the pump cell current produced by the pump cell. The controller may define a difference between a value of the pump cell-applied voltage on the control point and the value of the voltage applied to the pump cell determined using the voltage-to-current relation as a voltage correction value and store the voltage correction value in a backup memory.

The controller may correct the voltage-to-current relation using a value of the pump cell-applied voltage on the control point.

The gasses admitted into the gas chamber may be exhaust gasses of an automotive engine. The controller may work to control the voltage to be applied to the pump cell at startup or rest of the engine.

According to the fourth aspect of the invention, there is provided a gas concentration measuring apparatus which comprises: (a) a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current indicating a concentration of a specified gas component contained in the gasses having passed through the pump cell, and a monitor cell working to produce a monitor cell current indicative of a concentration of residual oxygen molecules within the gas chamber, the sensor cell having a given pump cell applied voltage-to-sensor cell current characteristic in which the sensor cell current changes as a function of a pump cell-applied voltage applied to the pump cell; (b) a first circuit working to determine a value of the pump cell-applied voltage when a value of the sensor cell current changes greatly at a given rate in the pump cell applied voltage-to-sensor cell current characteristic; and (c) a second circuit which works to determine a degree of deterioration of the gas concentration sensor based on the value of the pump cell-applied voltage when the value of the sensor cell current changes greatly.

In the preferred mode of the invention, the second circuit determines that the degree of deterioration has increased as the value of the pump cell-applied voltage when the value of the sensor cell current changes greatly is shifted to the higher voltage side.

The gasses admitted into the gas chamber may be exhaust gasses of an automotive engine. In this case, the second circuit works to determine the degree of deterioration at startup or rest of the engine.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
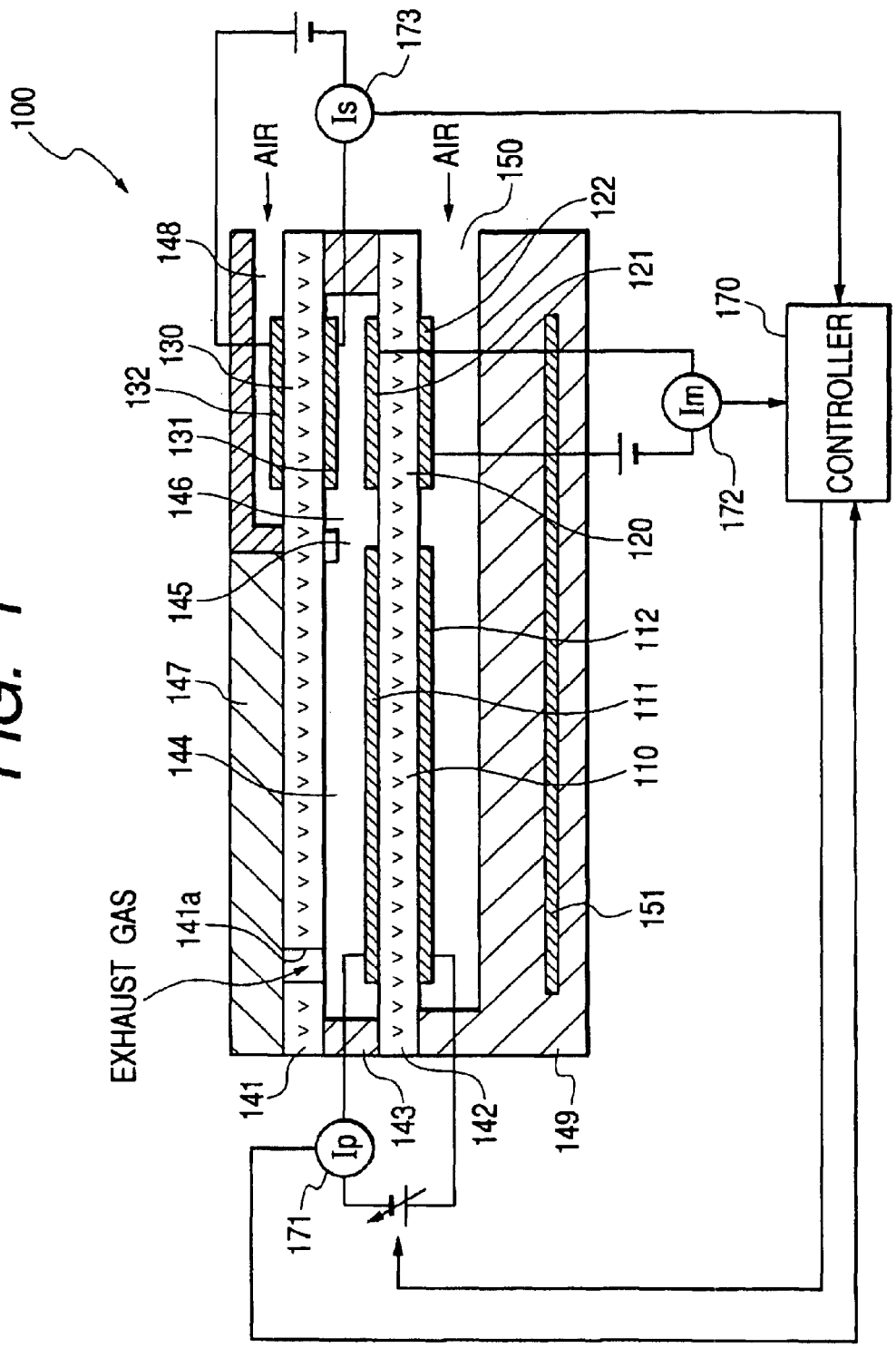
FIG. 1 is a block diagram which shows a gas concentration measuring apparatus according to the first embodiment of the invention.

Referring now to the drawings, wherein like numbers refer to like parts in several views, particularly to FIG. 1, there is shown a gas concentration measuring apparatus according to the first embodiment of the invention which may be used with an automotive control system designed to control the quantity of fuel injected into an internal combustion engine as a function of an output of the gas concentration measuring apparatus under feedback (F/B) control to bring the air-fuel (A/F) ratio into agreement with a target value. The gas concentration measuring apparatus uses a composite limiting current gas sensor which has a three-cell structure capable of measuring concentrations of oxygen ($O_2$) and nitrogen oxide (NOx) contained in exhaust gasses of the internal combustion engine simultaneously.

The gas concentration measuring apparatus, as shown in FIG. 1, generally includes a gas concentration sensor 100, a microcomputer or controller 170, and current detectors 171, 172, and 173 (e.g., ammeters).

The following discussion will refer to an example in which the gas concentration sensor 100 is installed in an exhaust pipe of an automotive internal combustion engine.

The gas concentration sensor 100 includes generally solid electrolyte plates 141 and 142 made of an oxygen ion-conducting material. The solid electrolyte plates 141 and 142 are laid to overlap each other at a given interval through a spacer 143 made of an insulating material, such as alumina. The solid electrolyte plate 141 has formed therein a pinhole 141a through which exhaust gasses flowing around the gas concentration sensor 100 are admitted into a first chamber 144. The first chamber 144 communicates with a second chamber 146 through an orifice 145 working as a diffusion path. On the solid electrolyte plate 141, a porous diffusion layer 147 is formed.

The solid electrolyte plate 142 has formed therein a pump cell 110 and a monitor cell 120. The pump cell 110 works to dissociate or ionize and pump thereinto oxygen molecules ($O_2$) contained the exhaust gasses admitted into the first chamber 144 and discharge them for measuring the concentration of oxygen ($O_2$) contained in the exhaust gasses and also to dissociate or ionize and pump oxygen molecules ($O_2$) within an air passage 150 into the first chamber 144 when the concentration of oxygen within the first chamber 144 is lower than a given level for keeping the concentration of oxygen within the first chamber 144 at the given level. The monitor cell 120 works to produce an electromotive force or current upon application of the voltage as a function the concentration of oxygen ($O_2$) within the second chamber 146. The pump cell 110 has a pair of upper and lower electrodes 111 and 112 disposed on opposed surfaces thereof. The upper electrode 111 is exposed to the first chamber 144 and inactive with respect to NOx, that is, hardly decomposes NOx. Similarly, the monitor cell 120 has a pair of upper and lower electrodes 121 and 122 disposed on opposed surfaces thereof. The upper electrode 121 is exposed to the second chamber 146 and inactive with respect to NOx, like the electrode 111. The pump cell 110 and the monitor cell 120 work to pump $O_2$ molecules contained in the exhaust gasses out of the first and second chambers 144 and 146 and discharge them to the air passage 150 through the electrodes 112 and 122.

A sensor cell 130 is formed in the solid electrolyte plate 141 opposite the monitor cell 120 and has a pair of upper and lower (with respect to FIG. 1) electrodes 132 and 131 formed on opposed surfaces thereof. The sensor cell 130 serves to measure the concentration of NOx contained in the exhaust gasses having passed through the pump cell 110 and discharge the oxygen produced when NOx is decomposed within the second chamber 146 to the air passage 148 through the electrode 132.

An insulating layer 149 is disposed on a lower surface, as viewed in the drawing, of the solid electrolyte plate 142 to define the air passage 150. The insulating layer 149 has embedded therein a heater 151 for heating the whole of the sensor 100 up to a given temperature.

In operation, when exhaust gasses containing $O_2$, NOx, $CO_2$, and $H_2O$ is entering the first chamber 144 through the porous diffusion layer 147 and the pinhole 141a and are passing through the pump cell 110, application of voltage to the pump cell 110 through the electrodes 111 and 112 causes the exhaust gasses to undergo dissociation, so that the oxygen is pumped into or out of the first chamber 144 as a function of the concentration of oxygen ($O_2$) within the first chamber 144. Since the upper electrode 111 of the pump cell 110 is, as described above, made of a metal which hardly dissolves NOx, when the concentration of oxygen within the first chamber 144 is higher than a desired level, only $O_2$ molecules within the first chamber 144 are ionized by the pump cell 110 without decomposing NOx, which are, in turn, discharged to the air passage 150. This causes a current (which will also be referred to as a pump cell current below) to be produced in the pump cell 110 as a function of the oxygen content of the exhaust gasses. EP 0 987 546 A2, assigned to the same assignee as that of this application, teaches control of an operation of this type of gas sensor, disclosure of which is incorporated herein by reference.

The $O_2$ molecules in the exhaust gasses are usually not dissociated by the pump cell 110 completely, so that residual $O_2$ molecules flow into the second chamber 146 and reach the monitor cell 120. The application of a given constant voltage to the monitor cell 120 through the electrodes 121 and 122 causes an output (which will also be referred to as a monitor cell current below) to be produced as a function of the concentration of the residual oxygen. The application of a given constant voltage to the sensor cell 130 through the electrodes 131 and 132 causes NOx molecules contained in the exhaust gasses to be decomposed or reduced, so that oxygen ions are produced and discharged to the air passage 148, thereby causing a current (also referred to as a sensor cell current or a NOx current below) to flow through the sensor 130 as a function of the concentration of NOx within the second chamber 146.

The controller 170 is implemented by a typical arithmetic logic unit consisting of a CPU, a memory, an A/D converter, a D/A converter, etc.

Power supply circuits are, as clearly shown in the drawing, provided one for each of the pump cell 110, the monitor cell 120, and the sensor cell 130. The power supply circuits include voltage sources for applying the voltages Vp, Vm, and Vs to the pump cell 110, the monitor cell 120, and the sensor cell 130 and the current detectors 171, 172, and 173, respectively. The voltage Vp applied to the pump cell 110 is, as described above, variably controlled by the controller 170. The voltages Vm and Vs applied to the monitor cell 120 and the sensor cell 130 are at constant levels. The current detector 171 measures the pump cell current Ip produced by the pump cell 110 and provides a signal indicative thereof to the controller 170. The current detector 172 measures the monitor cell current Im produced by the monitor cell 120 and provides a signal indicative thereof to the controller 170. The current detector 173 measures the sensor cell current Is produced by the sensor cell 130 and provides a signal indicative thereof to the controller 170.

The controller 170 receives the output from the current detector 171 of the pump cell 110 indicative of the pump cell current Ip and determines the concentration of oxygen ($O_2$) in the exhaust gasses and also determines a value of the pump cell-applied voltage Vp to be applied to the pump cell 110 using a preselected target applying voltage line, as will be described later in detail. The controller 170 also receives the output from the current detector 172 of the monitor cell 120 indicative of the monitor cell current Im to determine the quantity of oxygen remaining in the second chamber 146. The controller 170 also receives the output from the current detector 173 of the sensor cell 130 indicative of the sensor cell current Ip and determines the concentration of NOx contained in the exhaust gasses. The controller 170 may use the monitor cell current Im in correcting the value of the pump cell-applied voltage Vp to the pump cell 110 so as to keep the concentration of oxygen within the second chamber 146 constant or correcting the sensor cell current Is to eliminate a noise or error added thereto arising from the oxygen remaining within the second chamber 146.

Figure 2A:
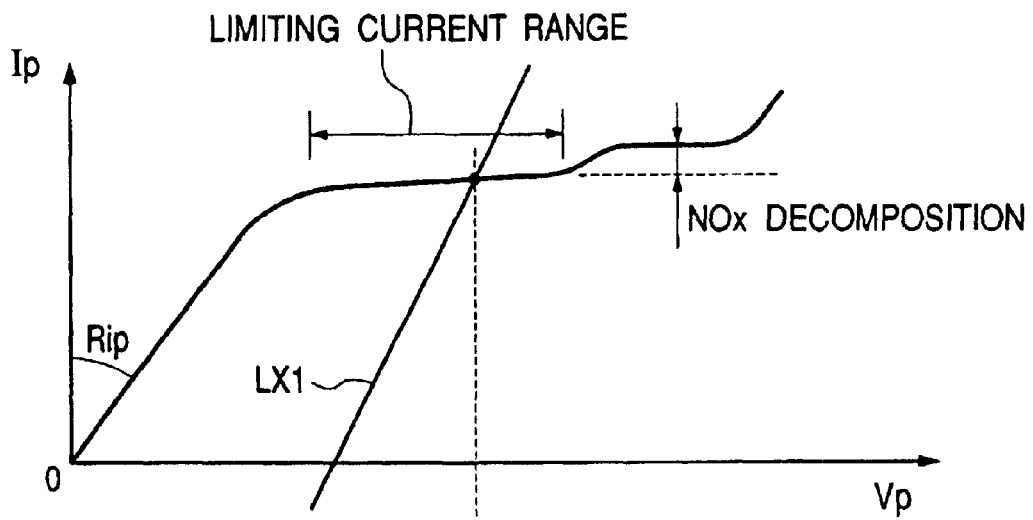
FIG. 2(a) shows a relation between a current output of a pump cell and a value of voltage to be applied to the pump cell and a target applying voltage line used to determine a target value of voltage to be applied to the pump cell.
Figure 2B:
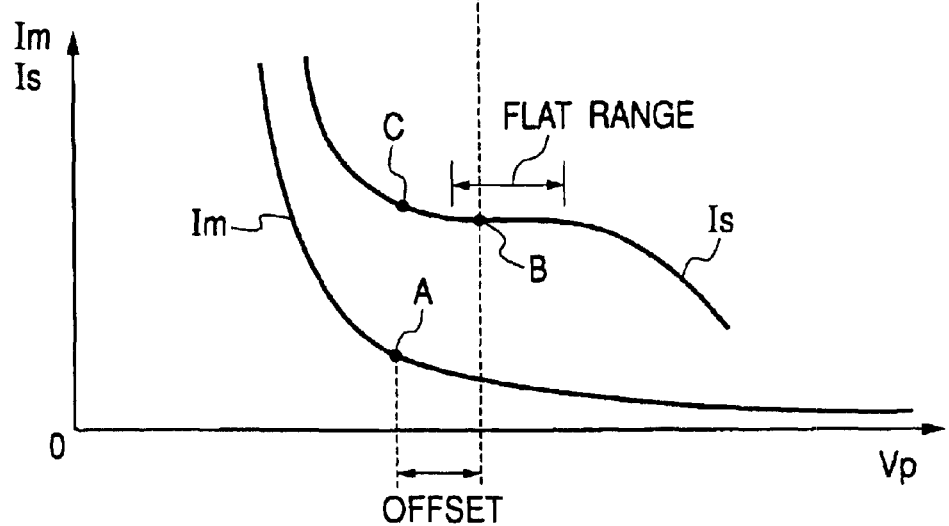
FIG. 2(b) shows relations between a current output of a monitor cell and a value of voltage applied to a pump cell and between a current output of a sensor cell and the value of voltage applied to the pump cell.

FIG. 2(a) shows a Vp-Ip relation between the voltage applied to the pump cell 110 (i.e., the pump cell-applied voltage Vp) and the pump cell current Ip. FIG. 2(b) shows a Vp-Im relation between the pump cell-applied voltage Vp and the monitor cell current Im and a Vp-Is relation between the pump cell-applied voltage Vp and the sensor cell current Is. Note that FIGS. 2(a) and 2(b) illustrate for cases where the concentrations of $O_2$ and NOx are constant, respectively.

The pump cell 110, as described above, produces the pump cell current Ip, changing, as shown in FIG. 2(a), upon application of the pump cell-applied voltage Vp. The pump cell current Ip contains a limiting current. A straight segment of a curve inclined slightly upward with respect to a V-axis (i.e., abscissa axis) indicates a limiting current range in which the limiting current is developed by the pump cell 110. The limiting current range is shifted to the positive side (i.e., a higher voltage side) of voltage applied to the pump cell 110 as the concentration of oxygen increases. A portion of the curve lower in voltage than the limiting current range indicates a resistance-dependent range. The portion extends upward at an inclination substantially depending upon an impedance Rip of the pump cell 110 (i.e., the solid electrolyte plate 142). The impedance Rip will also be referred to as a cell impedance Rip below.

The gas concentration measuring apparatus of this embodiment stores therein a V-I map, as shown in FIG. 2(a), and monitors the pump cell current Ip to determine a target value of the pump cell-applied voltage Vp to be applied to the pump cell 110 by look-up using the V-I map. The V-I map has a target applying voltage line LX1 used in determining the target value of the pump cell-applied voltage Vp. The upper pump cell electrode 111 of the pump cell 110 exposed to the first chamber 144 is, as described above, made of material which hardly decomposes NOx, so that NOx molecules in the exhaust gasses are hardly decomposed, but if the voltage applied to the pump cell 110 exceeds a certain upper limit, it will cause the NOx molecules to be decomposed, thereby producing an error in the pump cell current Ip (i.e., the limiting current) outputted from the pump cell 110. In practice, the target applying voltage line LX1 is so defined as to keep the concentration of oxygen ($O_2$) within the first chamber 144 at a lower level (near the stoichiometric). For instance, the target applying voltage line LX1 is so defined that a small quantity of $O_2$ (e.g., several ppm to several tens ppm) remains in the first chamber 144.

The Vp-Im relation between the pump cell-applied voltage Vp and the monitor cell current Im in FIG. 2(b) shows that within a range where the pump cell-applied voltage Vp is lower in level, the monitor cell current Im increases greatly with a decrease in pump cell-applied voltage Vp, but it decreases and reaches almost a constant level when the pump cell-applied voltage Vp enters a higher level range. Specifically, as apparent from FIG. 2(a), within the lower pump cell-applied voltage range (i.e., the resistance-dependent range), the pump cell current Ip is lower in level, so that the quantity of oxygen remaining within the first chamber 144 increases. Within the limiting current range of the pump cell 110, the pump cell current Ip is kept almost constant, so that the quantity of oxygen remaining within the first chamber 144 is kept constant. The monitor cell current Im, therefore, changes, as shown in FIG. 2(b), as a function of the pump cell-applied voltage Vp. The curve indicating a change in the monitor cell current Im has an inflection point A at which a rate of the change in the monitor cell current Im changes greatly. The inflection point A may be defined at a point where an inclination of the curve meets a preselected reference rate of the change in the monitor cell current Im.

The Vp-Is relation between the pump cell-applied voltage Vp and the sensor cell current Is has a flat range within which the sensor cell current Is is kept almost constant regardless of the pump cell-applied voltage Vp. Therefore, if the pump cell-applied voltage Vp is adjusted to a level B (which will also be referred to as a controlled point below), it is possible to measure the concentration of NOx in the exhaust gasses accurately. In this case, the inflection point A of the Vp-Im curve is away from the flat range of the sensor cell current Is. Specifically, the inflection point A is offset from the controlled point B. The offset between the inflection point A and the controlled point B is the value fixed for each type of gas sensor.

A change in impedance Rip of the pump cell 110 arising from a unit-to-unit difference or aging of the gas concentration sensor 100 will be described below with reference to FIGS. 3(a) to 4(b). Solid lines in FIGS. 3(a) to 4(b) indicate the V-I curves as illustrated in FIGS. 2(a) and 2(b). Broken lines indicate V-I curves when the pump cell impedance Rip increases or decreases.

Figure 3A:
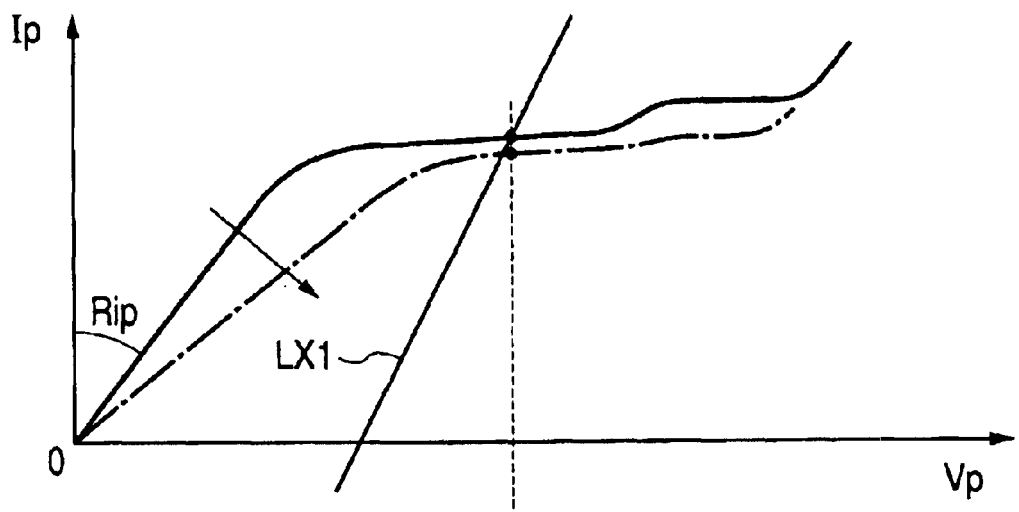
FIG. 3(a) shows a relation between a current output of a pump cell and a value of voltage to be applied to the pump cell which is shifted due to, for example, aging of a gas concentration sensor.
Figure 3B:
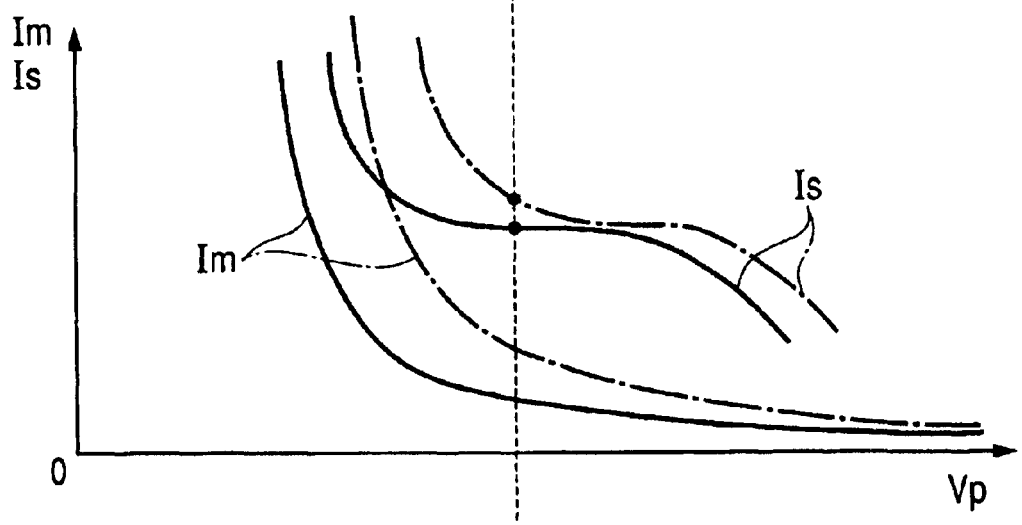
FIG. 3(b) shows relations between a current output of a monitor cell and a value of voltage applied to a pump cell and between a current output of a sensor cell and the value of voltage applied to the pump cell which are shifted due to, for example, aging of a gas concentration sensor.

When the impedance Rip of the pump cell 110 increases, it will cause the inclination of the Vp-Ip curve of FIG. 3(a) to decrease, so that the pump cell current Ip decreases. This causes the quantity of oxygen remaining within the first chamber 144 to increase. The monitor cell current Im and the sensor cell current Is, thus, change, as indicated by the broken lines of FIG. 3(b). Specifically, the sensor cell current Is increases, thus resulting in an increase in error in determining the concentration of NOx using the sensor cell current Is.

Figure 4A:
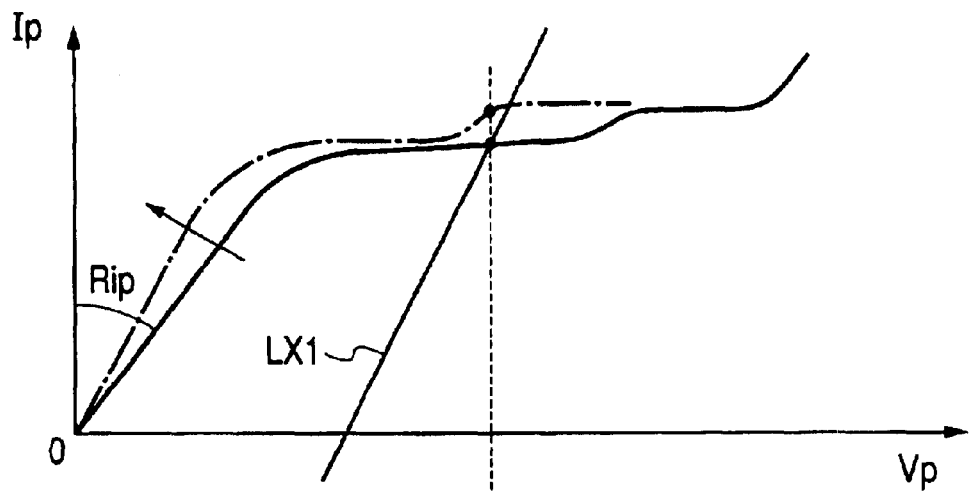
FIG. 4(a) shows a relation between a current output of a pump cell and a value of voltage to be applied to the pump cell which is shifted due to a change in impedance of a gas concentration sensor.
Figure 4B:
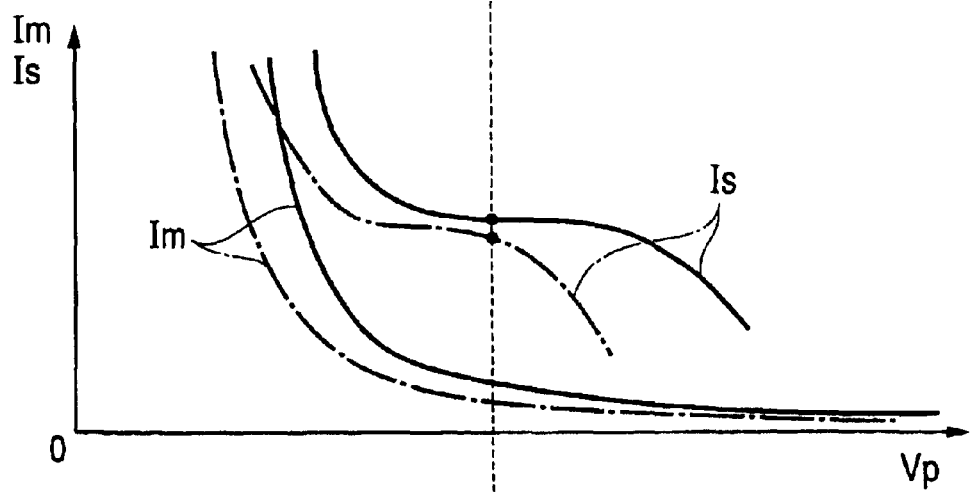
FIG. 4(b) shows relations between a current output of a monitor cell and a value of voltage applied to a pump cell and between a current output of a sensor cell and the value of voltage applied to the pump cell which are shifted due to an increase in quantity of oxygen remaining within a gas chamber of a gas concentration sensor.

Conversely, when the pump cell impedance Rip is decreased, it will cause the inclination of the Vp-Ip curve to increase, as indicated by the broken line in FIG. 4(a), so that the pump cell current Ip increases. This causes the quantity of oxygen remaining within the first chamber 144 to decrease. The monitor cell current Im and the sensor cell current Is, thus, change, as indicated by the broken lines of FIG. 4(b). Specifically, the sensor cell current Is decreases, thus resulting in an increase in error in determining the concentration of NOx using the sensor cell current Is.

As apparent from the above discussion, an undesirable change in impedance Rip of the pump cell 110 results in decreased accuracy of measuring the concentration of NOx using the sensor cell current Is produced by the sensor cell 130. This is due to the fact that the change in pump cell impedance Rip results in a shift in the flat range of the sensor cell current Is, which leads to an increase in error of the sensor cell current Is. In order to avoid this problem, the gas concentration measuring apparatus of this embodiment is designed base on the fact that a correlation between the inflection point A of the Vp-Im curve indicating a change in the monitor cell current Im in terms of a change in the pump cell-applied voltage Vp and the flat range of the sensor cell current Is is fixed regardless of a change in pump cell impedance Rip and works to locate the inflection point A of the monitor cell current Im and control the pump cell-applied voltage Vp based thereon.

Specifically, a change in quantity of oxygen remaining within the first chamber 144 results in a change in the inflection point A of the monitor cell current Im. The gas concentration measuring apparatus locates the inflection point A, adds an offset value to a value of the pump cell-applied voltage Vp corresponding to the inflection point A, and defines it as a control point to control the pump cell-applied voltage Vp within the flat range of the sensor cell current Is, thereby keeping the accuracy of measuring the concentration of NOx using the sensor cell current Is.

Figure 5:
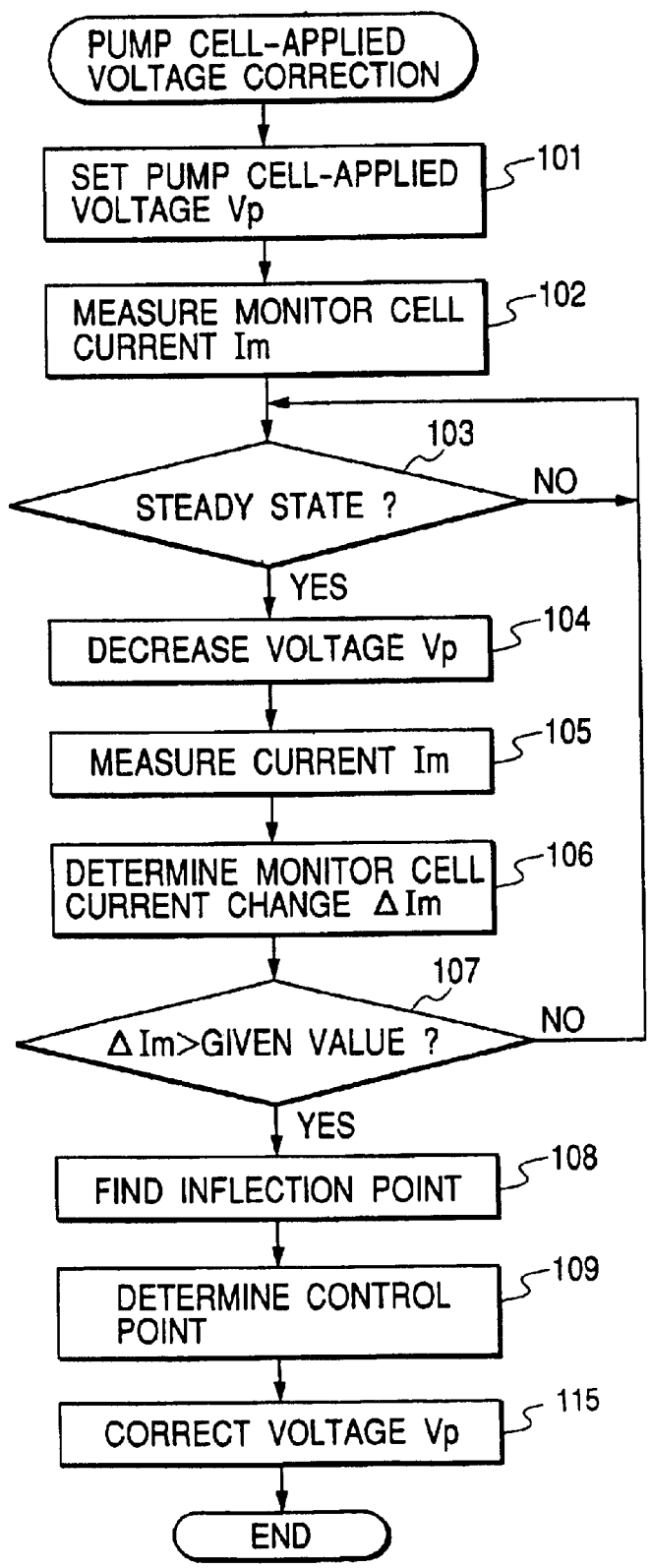
FIG. 5 is a flowchart of a program executed to correct a value of voltage to be applied to a pump cell in the first exemplary non-limiting embodiment of the invention.

Control of the pump cell-applied voltage Vp to be applied to the pump cell 110 will be described below in detail. FIG. 5 is a flowchart of a program to correct the pump cell-applied voltage Vp which is executed by the controller 170 at a regular interval of, for example, several seconds. This pump cell-applied voltage correction time is shifted from a gas concentration measuring time when the concentration of NOx is measured cyclically. Specifically, during the gas concentration measuring time, the pump cell-applied voltage Vp is determined as a function of the pump cell current Ip using the target applying voltage line LX1 to measure the concentration of NOx in a cycle of, for example, 4 msec. When the pump cell-applied voltage correction time is entered, the gas concentration measuring apparatus works to prohibit the measurement of the concentration of NOx and correct the pump cell-applied voltage Vp as a function of a unit-to-unit difference or degree of aging of the gas concentration sensor 100.

After entering the program of FIG. 5, the routine proceeds to step 101 wherein an initial value of the pump cell-applied voltage Vp is determined by look-up using the target applying voltage line LX1 of FIG. 2(a) as a function of the pump cell current Ip as measured instantaneously and applied to the pump cell 110.

The routine proceeds to step 102 wherein the monitor cell current Im produced upon the application of the initial value of the pump cell-applied voltage Vp to the pump cell 110 is measured.

The routine proceeds to step 103 wherein it is determined whether the gas concentration sensor 100 is in a steady state or not. Specifically, if a change in the pump cell current Ip, that is, a change in concentration of oxygen in the exhaust gasses is kept below a given value for a preselected period of time, a YES answer is obtained meaning that the gas concentration sensor 100 is now in the steady state. The routine then proceeds to step 104 wherein the pump cell-applied voltage Vp applied to the pump cell 110 is decreased by a given value. Specifically, the pump cell-applied voltage Vp is decreased in a unit of 2 mV to 10 mV in each program cycle. The routine proceeds to step 105 wherein after converged following the change in pump cell-applied voltage Vp, the monitor cell current Im is measured.

The routine proceeds to step 106 wherein the value of the monitor cell current Im, as measured one program cycle earlier, is subtracted from that, as measured in this program cycle, to determine a monitor cell current change $\Delta$Im. The routine proceeds to step 107 wherein it is determined whether the monitor cell current change $\Delta$Im is greater than a predetermined value or not. If a NO answer is obtained meaning that the monitor cell current change $\Delta$Im is lower than the predetermined value, then the routine returns back to step 103 to decrease the pump cell-applied voltage Vp by the given value again in step 104 and measure the monitor cell current change $\Delta$Im again in step 106.

If a YES answer is obtained in step 107, then the routine proceeds to step 108 wherein the inflection point A of the monitor cell current Im is located based on the monitor cell current change $\Delta$Im, as determined in step 107 to be greater than the predetermined value, and a corresponding value of the pump cell-applied voltage Vp is determined.

The routine proceeds to step 109 wherein a given offset value is added to the value of the pump cell-applied voltage Vp at the inflection point A of the monitor cell current Im, as determined in step 108, to determine the control point of the pump cell-applied voltage Vp that is a reference voltage value to which the pump cell-applied voltage Vp is to be controlled. The routine proceeds to step 115 wherein the target applying voltage line LX1 is corrected using the control point as determined in step 109. For example, a voltage correction value is determined based on a difference between a value of the pump cell-applied voltage Vp at the control point and a value of the pump cell-applied voltage Vp determined using the target applying voltage line LX1 and stored in a backup memory, such as a backup RAM or a flash ROM, or used in correcting the target applying voltage line LX1. In this case, when the gas concentration measuring time is entered to measure the concentration of NOx, the controller 170 corrects the pump cell-applied voltage Vp using the voltage correction value to determine a final voltage to be applied to the pump cell 110 or determines the final voltage using the corrected target applying voltage line LX1.

Figure 6A:
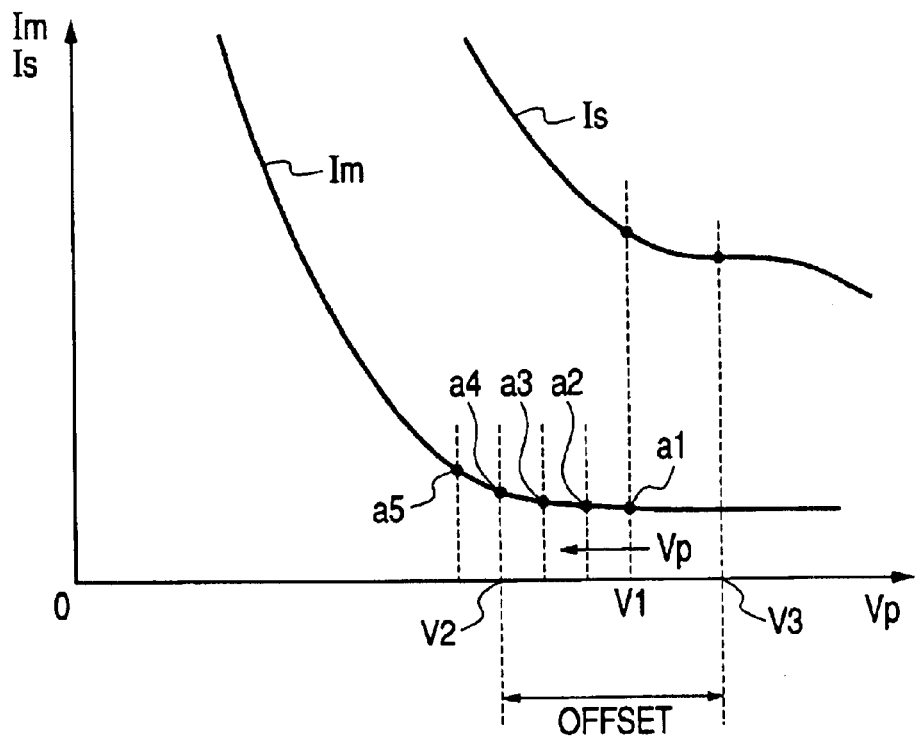
FIG. 6(a) is a graph which illustrates changes in monitor cell current to be measured when a pump cell-applied voltage changes stepwise in the first exemplary non-limiting embodiment of the invention.
Figure 6B:
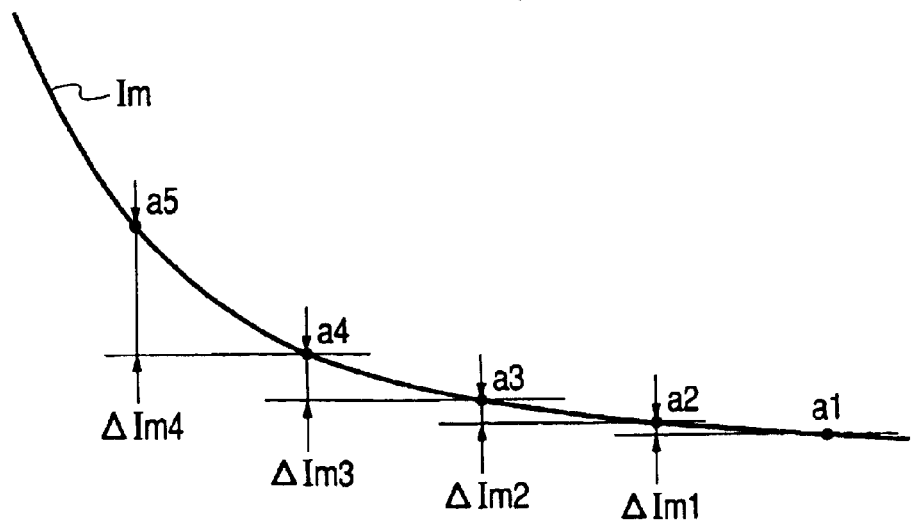
FIG. 6(b) is a partially enlarged view of FIG. 6(a) which illustrates a change in monitor cell current.

The operation of the controller 170 executed in the program of FIG. 5 will be exemplified below using FIGS. 6(a) and 6(b). FIG. 6(a) illustrates changes in monitor cell current Im and sensor cell current Is in terms of a change in pump cell-applied voltage Vp. FIG. 6(b) is a partially enlarged view of FIG. 6(a) which illustrates the change in monitor cell current Im.

It is assumed that the pump cell-applied voltage Vp is initially set to a voltage value V1, as shown in FIG. 6(a). The monitor cell current Im is measured at a point a1. Subsequently, the pump cell-applied voltage Vp is decreased in a unit of a preselected voltage level in one program cycle. The monitor cell current Im is measured at a point a2. In the shown case, a difference in monitor cell current Im between the points a1 and a2 (i.e., the monitor cell current change $\Delta$Im determined in step 106 of FIG. 5) is still lower than the predetermined value, therefore, the monitor cell current Im is further measured at the points a3, a4, and a5. The monitor cell current change $\Delta$Im is determined in step 107 as being greater than the predetermined value at the point a5. Referring to FIG. 6(b), the monitor cell current changes $\Delta$Im1 to $\Delta$Im3, as measured at points a2 to a4 are each lower than the predetermined value, so that a NO answer is obtained in step 107. The monitor cell current change $\Delta$Im4, as measured at the point a5, is greater than the predetermined value, so that a YES answer is obtained in step 107. The point a4 preceding the point a5 is defined in step 108 as the inflection point A of the monitor cell current Im. The given offset value is added to the value V2 of the pump cell-applied voltage Vp at the inflection point A (i.e., the point a4) to determine the control point (i.e., the value V3 of the pump cell-applied voltage Vp) that is a target voltage to which the pump cell-applied voltage Vp is corrected. Specifically, the value V3 of the pump cell-applied voltage Vp is applied to the pump cell 110, thereby causing the sensor cell current Is to be measured within the flat range. In this case, a difference between the value V3 and the value V1 of the pump cell-applied voltage Vp is defined in step 115 as the voltage correction value.

As apparent from the above discussion, the gas concentration measuring apparatus of this embodiment is designed to find the value of the pump cell-applied voltage Vp corresponding to the inflection point A of the monitor cell current Im and define it as the control point to which the pump cell-applied voltage Vp applied to the pump cell 110 is controlled to keep the sensor cell current Is within the flat range of the Vp-Is curve. This keeps the accuracy of determining the concentration of NOx using the sensor cell current Is free from the unit-to-unit difference and/or aging of the gas concentration sensor 100.

The gas concentration measuring apparatus may be designed to find the value of the pump cell-applied voltage Vp which corresponds to the inflection point C, as shown in FIG. 2(b), of the sensor cell current Is, not the monitor cell current Im and determine the control point to which the pump cell-applied voltage Vp is controlled.

Referring back to FIG. 2(b), like the Vp-Im curve of the monitor cell current Im, the Vp-Is curve of the sensor cell current Is also has an inflection point C at which the rate of a change in the sensor cell current Is changes greatly. The gas concentration measuring apparatus may also be designed to control the pump cell-applied voltage Vp based on a locational relation between the inflection point C and the flat range where the sensor cell current Is hardly changes free from a change in the pump cell-applied voltage Vp. Specifically, a change in quantity of oxygen remaining within the first chamber 144 results in a shift in the inflection point C. The pump cell-applied voltage Vp is corrected as a function of the shift in the inflection point C so that a target value of the pump cell-applied voltage Vp may lie within the flat range. This keeps the accuracy of measuring the concentration of NOx using the sensor cell current Is.

The above operation may be achieved by executing the program of FIG. 5 using the sensor cell current Is and a sensor cell current change ΔIs instead of the monitor cell current Im and the monitor cell current change ΔIm. Specifically, an initial value of the pump cell-applied voltage Vp is first determined by look-up using the target applying voltage line LX1 of FIG. 2(a) as a function of the pump cell current Ip as measured instantaneously. The pump cell-applied voltage Vp is then applied to the pump cell 110. A resulting value of the sensor cell current Is is measured. The pump cell-applied voltage Vp applied to the pump cell 110 is decreased in a unit of a given level, after which the sensor cell current Is is measured. The value of the sensor cell current Is, as measured one program cycle earlier, is subtracted from that, as measured in this cycle, to determine the sensor cell current change ΔIs. It is determined whether the sensor cell current change ΔIs is greater than a predetermined value or not. When the sensor cell current change ΔIs becomes greater than the predetermined value, the inflection point C of the sensor cell current Is is located based on the sensor cell current change ΔIs, as determined to be greater than the predetermined value, and a corresponding value of the pump cell-applied voltage Vp is determined. A given offset value is added to the value of the pump cell-applied voltage Vp at the inflection point C of the sensor cell current Is to determine the control point of the pump cell-applied voltage Vp that is a reference voltage value to which the pump cell-applied voltage Vp is to be controlled. Finally, the target applying voltage line LX1 is corrected using the control point in the same manner as described above. This also keeps the accuracy of measuring the concentration of NOx using the sensor cell current Is free from the unit-to-unit difference and aging of the gas concentration sensor 100.

A gas concentration measuring apparatus of the second embodiment will be described below which is different from the first embodiment in that the inflection point A is determined based on a change in monitor cell current Im from a value of the monitor cell current Im corresponding to an initial value of the pump cell-applied voltage Vp as determined using the target applying voltage line LX1. Other arrangements and operations are identical, and explanation thereof in detail will be omitted here.

Figure 7A:
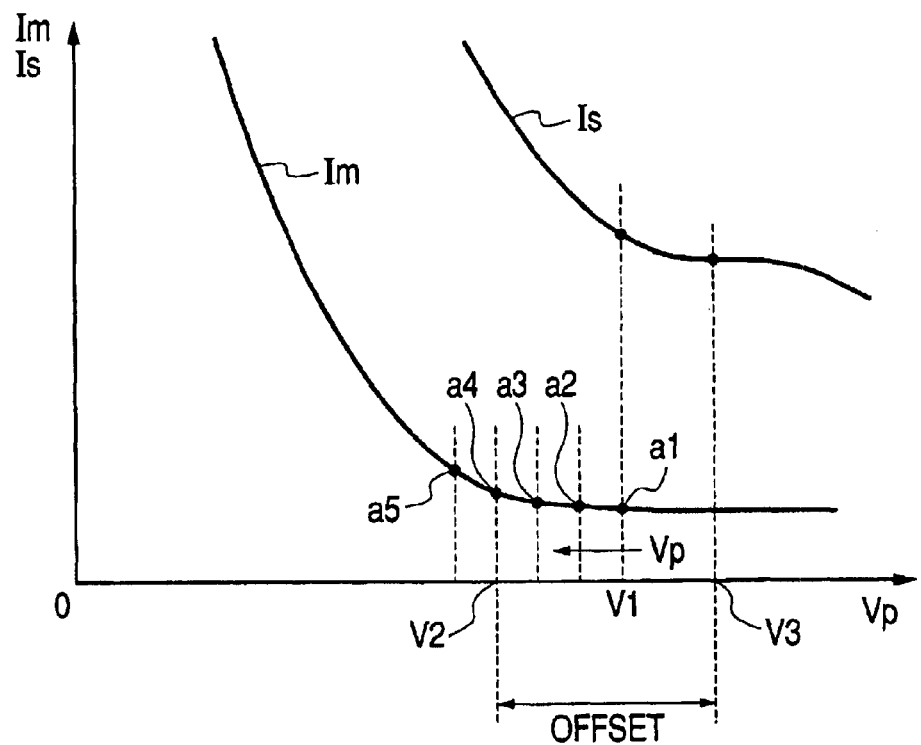
FIG. 7(a) is a graph which illustrates changes in monitor cell current to be measured when a pump cell-applied voltage is changed stepwise in the second embodiment of the invention.
Figure 7B:
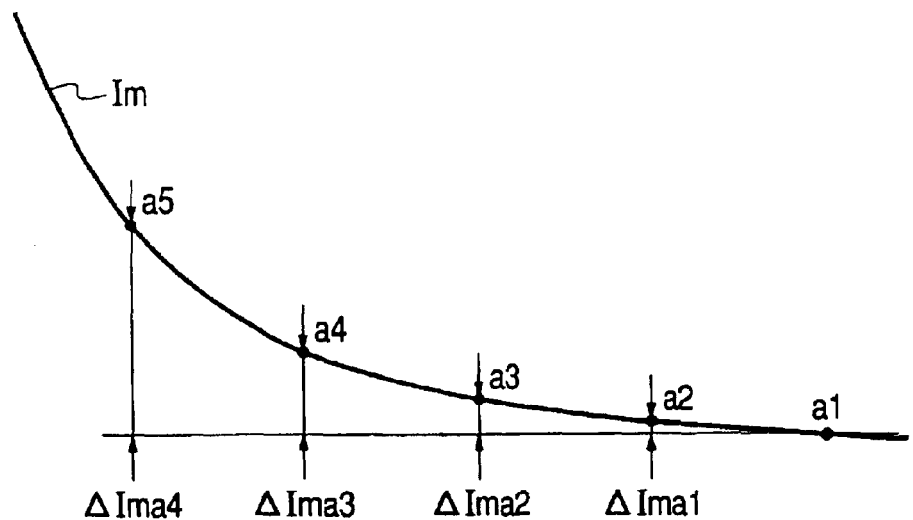
FIG. 7(b) is a partially enlarged view of FIG. 7(a) which illustrates a change in monitor cell current.

The operation of the controller 170 of the third embodiment will be exemplified below using FIGS. 7(a) and 7(b). FIG. 7(a) illustrates the monitor cell current Im and sensor cell current Is changing as a function of a change in pump cell-applied voltage Vp. FIG. 7(b) is a partially enlarged view of FIG. 7(a) which illustrates the change in monitor cell current Im.

It is assumed that the pump cell-applied voltage Vp is initially set to a voltage value V1, as shown in FIG. 7(a). The monitor cell current Im is measured at a point a1 and stored in a memory of the controller 170. Subsequently, the pump cell-applied voltage Vp is decreased in a unit of a preselected voltage level in one program cycle. In the shown case, differences ΔIma1, ΔIma2, ΔIma3, ΔIma4 in monitor cell current Im, as shown in FIG. 7(b), between the point a1 and the points a2, a3, a4, and a5 are determined in a sequence of program cycles, respectively. Specifically, the monitor cell current change ΔIma is determined by a change of the monitor cell current Im, as measured at each of the points a2, a3, a4, and a5 from the initial value of the monitor cell current Im, as measured at the point a1.

In this case, the monitor cell current change ΔIma4 is determined to be greater than the preselected value. The point a4 immediately preceding the point a5 is defined as the inflection point A. The given offset value is added to the value V2 of the pump cell-applied voltage Vp at the inflection point A (i.e., the point a4) to determine the control point (i.e., the value V3 of the pump cell-applied voltage Vp) that is a target voltage to which the pump cell-applied voltage Vp is corrected. Specifically, the value V3 of the pump cell-applied voltage Vp is applied to the pump cell 110, thereby causing the sensor cell current Is to be measured within the flat range.

Figure 8:
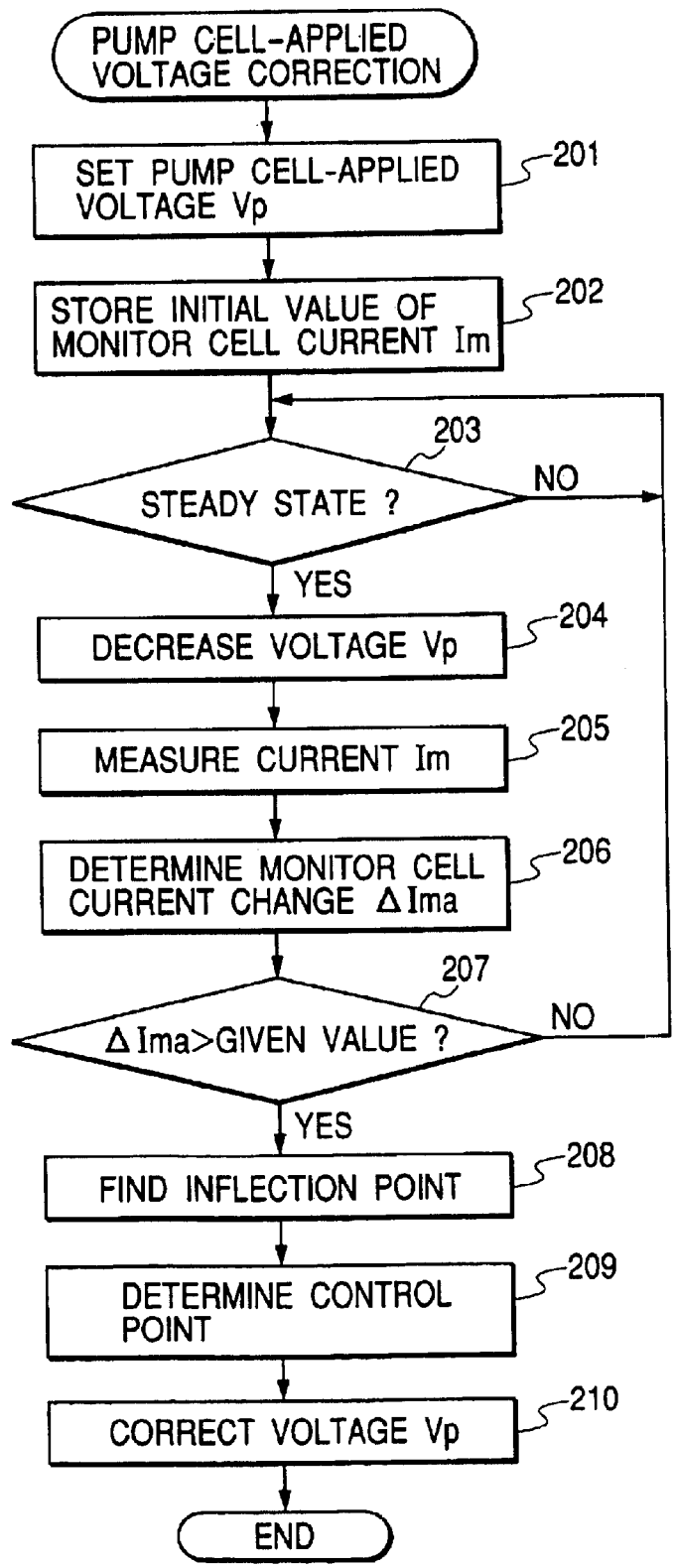
FIG. 8 is a flowchart of a program executed to correct a value of voltage to be applied to a pump cell in the second embodiment of the invention.

FIG. 8 is a flowchart of a program executed by the controller 170 to correct the pump cell-applied voltage Vp in this embodiment which is different from the one shown in FIG. 5 only in steps 202, 206, and 207. Other steps are identical, and explanation thereof in detail will be omitted here.

After an initial value of the pump cell-applied voltage Vp is determined in step 201, the routine proceeds to step 202 wherein the monitor cell current Im produced upon the application of the initial value of the pump cell-applied voltage Vp to the pump cell 110 is measured and stored in a memory such as a RAM installed in the controller 170. After the gas concentration sensor 100 is determined in step 203 to be in the steady state, the routine proceeds to step 204 wherein the pump cell-applied voltage Vp applied to the pump cell 110 is decreased by a given value. The routine proceeds to step 205 wherein after converged, the monitor cell current Im is measured.

The routine proceeds to step 206 wherein the value of the monitor cell current Im, as measured in step 202, is subtracted from that, as measured in step 205, to determine the monitor cell current change ΔIma. The routine proceeds to step 207 wherein it is determined whether the monitor cell current change ΔIma is greater than a predetermined value or not. If a NO answer is obtained meaning that the monitor cell current change ΔIma is lower than the predetermined value, then the routine returns back to step 203 to decrease the pump cell-applied voltage Vp by the given value again in step 204 and measure the monitor cell current change ΔIma again in step 206.

If a YES answer is obtained in step 207, then the routine proceeds to step 208 wherein the inflection point A of the monitor cell current Im is located in the manner, as described above, based on the monitor cell current change ΔIma, as determined in step 207 to be greater than the predetermined value, and a corresponding value of the pump cell-applied voltage Vp is determined.

The routine proceeds to step 209 wherein the given offset value is added to the value of the pump cell-applied voltage Vp at the inflection point A of the monitor cell current Im, as determined in step 208, to determine the control point of the pump cell-applied voltage Vp that is a reference voltage value to which the pump cell-applied voltage Vp is to be controlled. The routine proceeds to step 210 wherein the target applying voltage line LX1 is corrected using the control point as determined in step 209.

The gas concentration measuring apparatus of this embodiment has an additional advantage that the determination of the inflection point A using a change in monitor cell current Im from an initial value thereof serves to decrease an adverse effect of a noise contained in the monitor cell current Im.

The gas concentration measuring apparatus of the second embodiment may alternatively be designed to find the value of the pump cell-applied voltage Vp which corresponds to the inflection point C of the sensor cell current Is, not the monitor cell current Im and determine the control point to which the pump cell-applied voltage Vp is controlled.

The above operation may be achieved by executing the program of FIG. 8 using the sensor cell current Is and a sensor cell current change ΔIs instead of the monitor cell current Im and the monitor cell current change ΔIm. Specifically, an initial value of the pump cell-applied voltage Vp is first determined by look-up using the target applying voltage line LX1 of FIG. 2(a) as a function of the pump cell current Ip as measured instantaneously. The pump cell-applied voltage Vp is then applied to the pump cell 110. A resulting value of the sensor cell current Is is measured and stored in the memory of the controller 170. The pump cell-applied voltage Vp applied to the pump cell 110 is decreased in a unit of a given level. A resulting value of the sensor cell current Is is measured from which the initial value of the sensor cell current Is is subtracted to determine the sensor cell current change ΔIs. It is determined whether the sensor cell current change ΔIs is greater than a predetermined value or not. When the sensor cell current change ΔIs becomes greater than the predetermined value, the inflection point C of the sensor cell current Is is located based on the sensor cell current change ΔIs, as determined to be greater than the predetermined value, and a corresponding value of the pump cell-applied voltage Vp is determined. A given offset value is added to the value of the pump cell-applied voltage Vp at the inflection point C of the sensor cell current Is to determine the control point of the pump cell-applied voltage Vp that is a reference voltage value to which the pump cell-applied voltage Vp is to be controlled. Finally, the target applying voltage line LX1 is corrected using the control point in the same manner as described above. This also keeps the accuracy of measuring the concentration of NOx using the sensor cell current Is free from the unit-to-unit difference and aging of the gas concentration sensor 100.

Figure 9A:
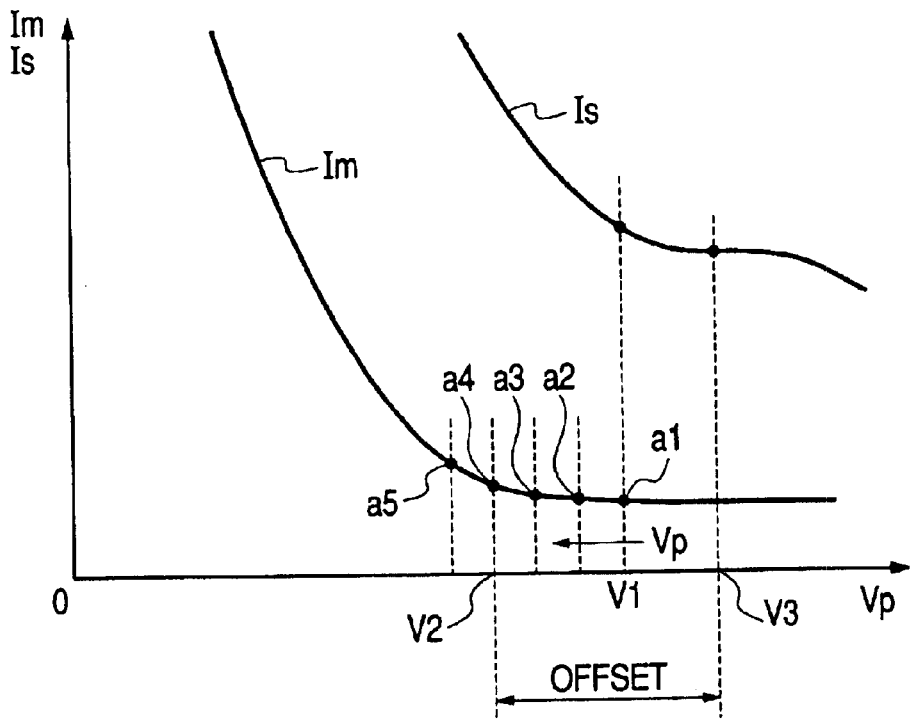
FIG. 9(a) is a graph which illustrates changes in monitor cell current to be measured when a pump cell-applied voltage is changed stepwise in the third embodiment of the invention.
Figure 9B:
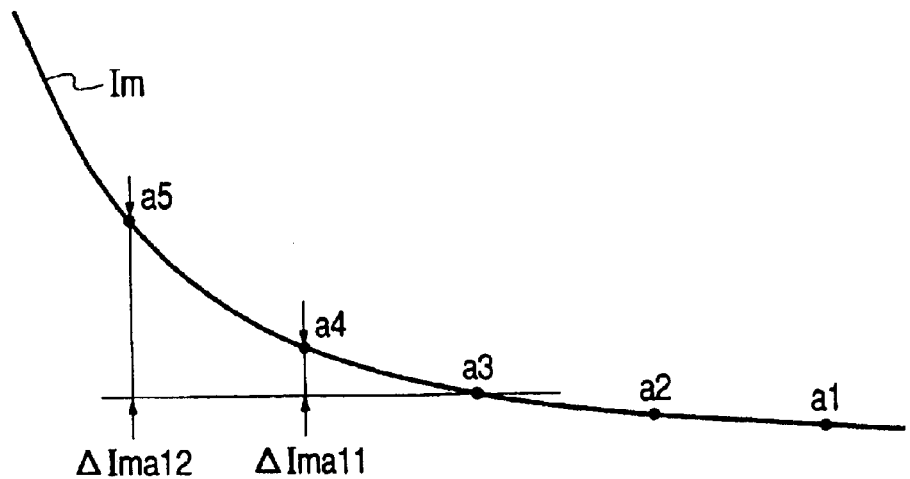
FIG. 9(b) is a partially enlarged view of FIG. 9(a) which illustrates a change in monitor cell current.

A gas concentration measuring apparatus of the third embodiment will be described below using FIGS. 9(a) and 9(b) which is designed to define a reference current value, as used in determining the monitor cell current change ΔIma, outside the flat range within which the monitor cell current Im hardly changes regardless of a change in the pump cell-applied voltage Vp and determine the inflection point A of the monitor cell current Im using the monitor cell current change ΔIma. FIG. 9(a) illustrates the monitor cell current Im and sensor cell current Is changing as a function of a change in pump cell-applied voltage Vp. FIG. 9(b) is a partially enlarged view of FIG. 9(a) which illustrates the change in monitor cell current Im.

Assuming that the pump cell-applied voltage Vp is initially set to a voltage value V1, as shown in FIG. 9(a), the monitor cell current Im is measured at a point a1. Subsequently, the pump cell-applied voltage Vp is decreased in a unit of a preselected voltage level in one program cycle. In the shown case, the pump cell-applied voltage Vp is decreased over a sequence of four program cycles, and resulting values of the monitor cell current Im are measured at points a2 to a5. The operations described so far are substantially identical with those in the above embodiments.

The value of the monitor cell current Im, as measured at the point a1, is stored in the memory of the controller 170. If a change in monitor cell current Im at each of the points a2 and a3 is small, the value of the monitor cell current Im stored in the memory is updated. Specifically, if the monitor cell current Im is, as clearly shown in FIG. 9(a), kept substantially constant prior to the point a3, it is determined as lying within the flat range of the Vp-Im curve. The value of the monitor cell current Im, as measured at the point a1 and stored in the memory, is updated, in sequence, to those measured at the points a2 and a3. In this case, the value of the monitor cell current Im as measured at the point a3 is finally stored in the memory as the reference current value. Next, based on the reference current, the monitor cell current change ΔIma is determined.

Specifically, in the shown case, monitor cell current changes ΔIma11 and ΔIma12 that are differences between the reference current value (i.e., the value of the monitor cell current Im as measured at the point a3) and the value of the monitor cell current Im as measured at the point a4 and between the reference current value and the value of the monitor cell current Im as measured at the point a5 are calculated. If the monitor cell current change ΔIma12 is greater than a given value, the point a4 preceding the point a5 is defined as the inflection point A of the monitor cell current Im. Next, a given offset value is, like the operations of FIGS. 5 and 8, added to the value V2 of the pump cell-applied voltage Vp at the inflection point A (i.e., the point a4) to determine the control point (i.e., the value V3 of the pump cell-applied voltage Vp) that is a target voltage to which the pump cell-applied voltage Vp is corrected.

Figure 10:
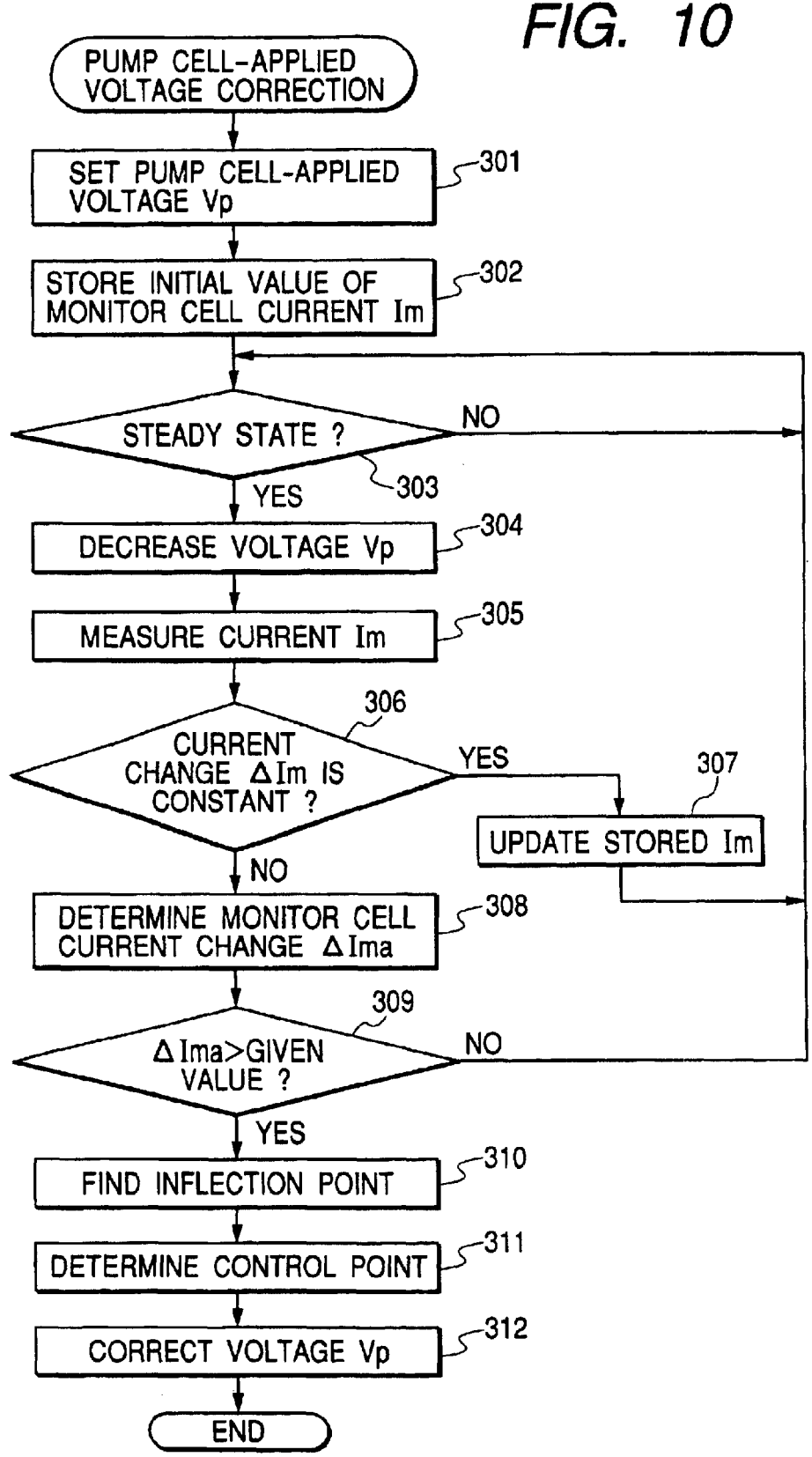
FIG. 10 is a flowchart of a program executed to correct a value of voltage to be applied to a pump cell in the third embodiment of the invention.

FIG. 10 is a flowchart of a program executed by the controller 170 to correct the pump cell-applied voltage Vp in the third embodiment which is different from the one shown in FIG. 8 only in steps 306 and 307. Other steps are identical, and explanation thereof in detail will be omitted here.

After an initial value of the pump cell-applied voltage Vp is determined in step 301, the routine proceeds to step 302 wherein the monitor cell current Im produced upon the application of the initial value of the pump cell-applied voltage Vp to the pump cell 110 is measured and stored in the memory installed in the controller 170. After the gas concentration sensor 100 is determined in step 303 to be in the steady state, the routine proceeds to step 304 wherein the pump cell-applied voltage Vp applied to the pump cell 110 is decreased by a given value. The routine proceeds to step 305 wherein after converged, the monitor cell current Im is measured.

The routine proceeds to step 306 wherein it is determined whether the rate of a change in monitor cell current Im arising from the decreasing of the monitor cell current Im is almost constant or not. For instance, if the change in monitor cell current Im is less than 10% thereof, then the routine proceeds to step 307 wherein the value of the monitor cell current Im stored in the memory is updated to the latest value thereof. The routine returns back to step 303.

If a NO answer is obtained in step 306 meaning that the value of the monitor cell current Im has been shifted outside the flat range, then the routine proceeds to step 308 wherein the value of the monitor cell current Im stored in the memory is subtracted from that as measured in step 305 of this program cycle to determine the monitor cell current change ΔIma. The routine proceeds to step 309 wherein it is determined whether the monitor cell current change ΔIma is greater than a predetermined value or not. If a NO answer is obtained meaning that the monitor cell current change ΔIm is lower than the predetermined value, then the routine returns back to step 303 to decrease the pump cell-applied voltage Vp by the given value again in step 304 and measure the monitor cell current change ΔIm again in step 308.

If a YES answer is obtained in step 309, then the routine proceeds to step 310 wherein the inflection point A of the monitor cell current Im is located in the manner, as described above, and a corresponding value of the pump cell-applied voltage Vp is determined.

The routine proceeds to step 311 wherein the given offset value is added to the value of the pump cell-applied voltage Vp at the inflection point A of the monitor cell current Im, as determined in step 310, to determine the control point of the pump cell-applied voltage Vp that is a reference voltage value to which the pump cell-applied voltage Vp is to be controlled. The routine proceeds to step 312 wherein the target applying voltage line LX1 is corrected using the control point as determined in step 311.

The gas concentration measuring apparatus of this embodiment has an additional advantage that the determination of the inflection point A using a change in monitor cell current Im, as determined outside the flat range of the monitor cell current Im, serves to decrease an adverse effect of a noise contained in the monitor cell current Im. Particularly, the inflection point A is determined based on the value of the monitor cell current Im in a range within which the monitor cell current Im changes greatly, thus improving the accuracy of measuring the concentration of NOx free from changes in monitor cell current Im within the flat range.

The gas concentration measuring apparatus of the third embodiment may alternatively be designed to find the value of the pump cell-applied voltage Vp which corresponds to the inflection point C of the sensor cell current Is, not the monitor cell current Im and determine the control point to which the pump cell-applied voltage is controlled.

The above operation may be achieved by executing the program of FIG. 10 using the sensor cell current Is and a sensor cell current change ΔIsa instead of the monitor cell current Im and the monitor cell current change ΔIma. Specifically, an initial value of the pump cell-applied voltage Vp is first determined. The pump cell-applied voltage Vp is then applied to the pump cell 110. A resulting value of the sensor cell current Is is measured and stored in the memory of the controller 170. The value of the sensor cell current Is stored in the memory is updated until it lies within the flat range of the Vp-Is curve. The pump cell-applied voltage Vp applied to the pump cell 110 is decreased in a unit of a given level. A resulting value of the sensor cell current Is is measured from which the value of the sensor cell current Is stored in the memory is subtracted to determine the sensor cell current change ΔIsa. It is determined whether the sensor cell current change ΔIsa is greater than a predetermined value or not. When the sensor cell current change ΔIsa becomes greater than the predetermined value, the inflection point C of the sensor cell current Is is located based on the sensor cell current change ΔIsa, as determined to be greater than the predetermined value, and a corresponding value of the pump cell-applied voltage Vp is determined. A given offset value is added to the value of the pump cell-applied voltage Vp at the inflection point C of the sensor cell current Is to determine the control point of the pump cell-applied voltage Vp that is a reference voltage value to which the pump cell-applied voltage Vp is to be controlled. Finally, the target applying voltage line LX1 is corrected using the control point in the same manner as described above.

A gas concentration measuring apparatus of the fourth embodiment will be described below.

If the aging of the gas concentration sensor 100 results in an increase in the cell impedance Rip, and the Ip-Vp curve of the pump cell 110 is, as shown in FIG. 3(a), inclined, the quantity of oxygen remaining within the first chamber 144 increases undesirably. This may cause an initial value of the pump cell-applied voltage Vp to be set on a lower voltage side of the inflection point A of the monitor cell current Im. In this case, the gas concentration measuring apparatus of this embodiment works to increase the pump cell-applied voltage Vp and determine the inflection point A of the monitor cell Im.

Figure 11A:
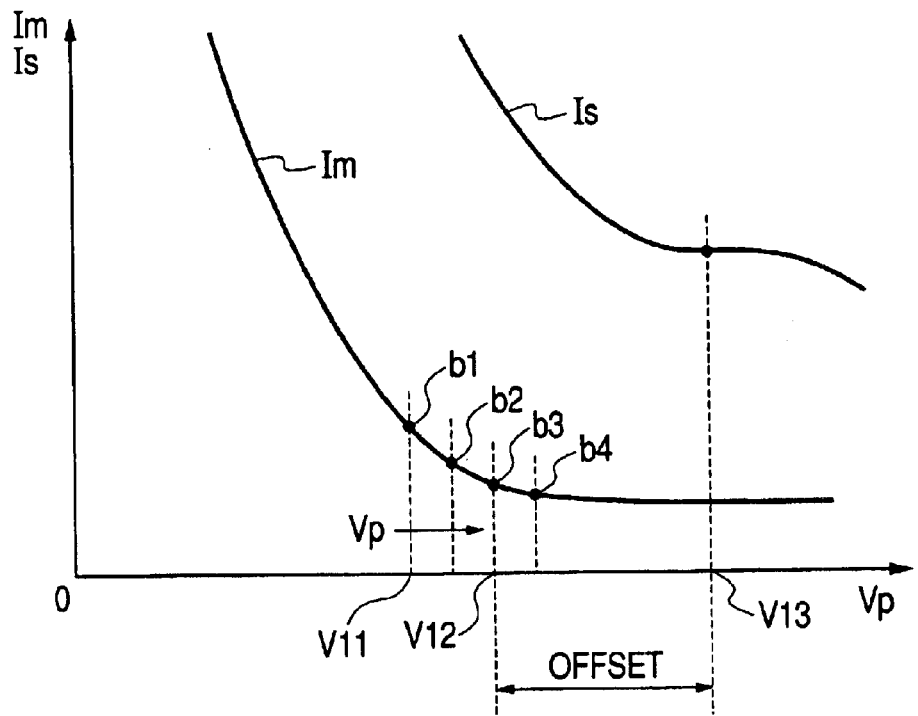
FIG. 11(a) is a graph which illustrates changes in monitor cell current to be measured when a pump cell-applied voltage is changed stepwise in the fourth embodiment of the invention.
Figure 11B:
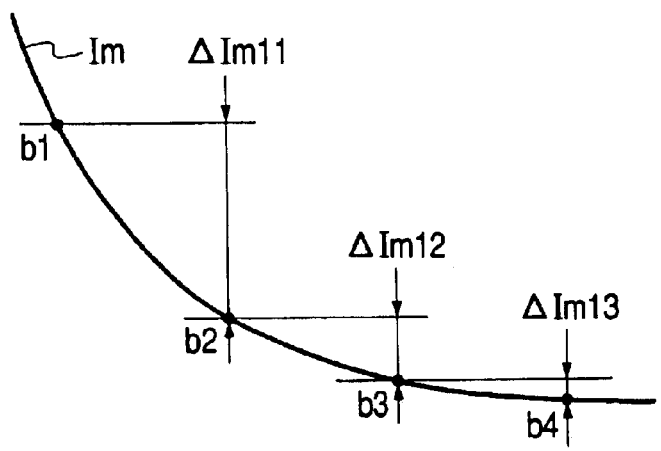
FIG. 11(b) is a partially enlarged view of FIG. 11(a) which illustrates a change in monitor cell current.

The operation of the gas concentration measuring apparatus of this embodiment will be described below using FIGS. 11(a) and 11(b). FIG. 11(a) illustrates the monitor cell current Im and sensor cell current Is changing as a function of a change in pump cell-applied voltage Vp. FIG. 11(b) is a partially enlarged view of FIG. 11(a) which illustrates the change in monitor cell current Im.

Assuming that the pump cell-applied voltage Vp is initially set to a voltage value V11, as shown in FIG. 11(a), using the target applying voltage line LX1, the monitor cell current Im is measured at a point b1. Subsequently, the pump cell-applied voltage Vp is increased in a unit of a preselected voltage level in one program cycle. In the shown case, the pump cell-applied voltage Vp is increased over a sequence of three program cycles, and resulting values of the monitor cell current Im are measured at points b2 to b4. In this example, a change in monitor cell current Im (i.e., the monitor cell current change ΔIm) that is a difference between the value of the monitor cell current Im, as measured at the point b4 and that, as measured at the point b3 becomes greater than a given value. Specifically, the monitor cell current changes ΔIm11 and ΔIm12, as clearly shown in FIG. 11(b), determined at the points b2 and b3 are less than the given value, while the monitor cell current change ΔIm13 determined at the point b4 is greater than the given value. In this case, the point b3 is defined as the inflection point A of the monitor cell current Im.

Next, a given offset value is added to the value V12 of the pump cell-applied voltage Vp at the inflection point A (i.e., the point b3) to determine the control point (i.e., the value V13 of the pump cell-applied voltage Vp) that is a target voltage to which the pump cell-applied voltage Vp is corrected. This enables the sensor cell current Is to be measured within the flat range of the Vp-Is curve thereof.

Figure 12:
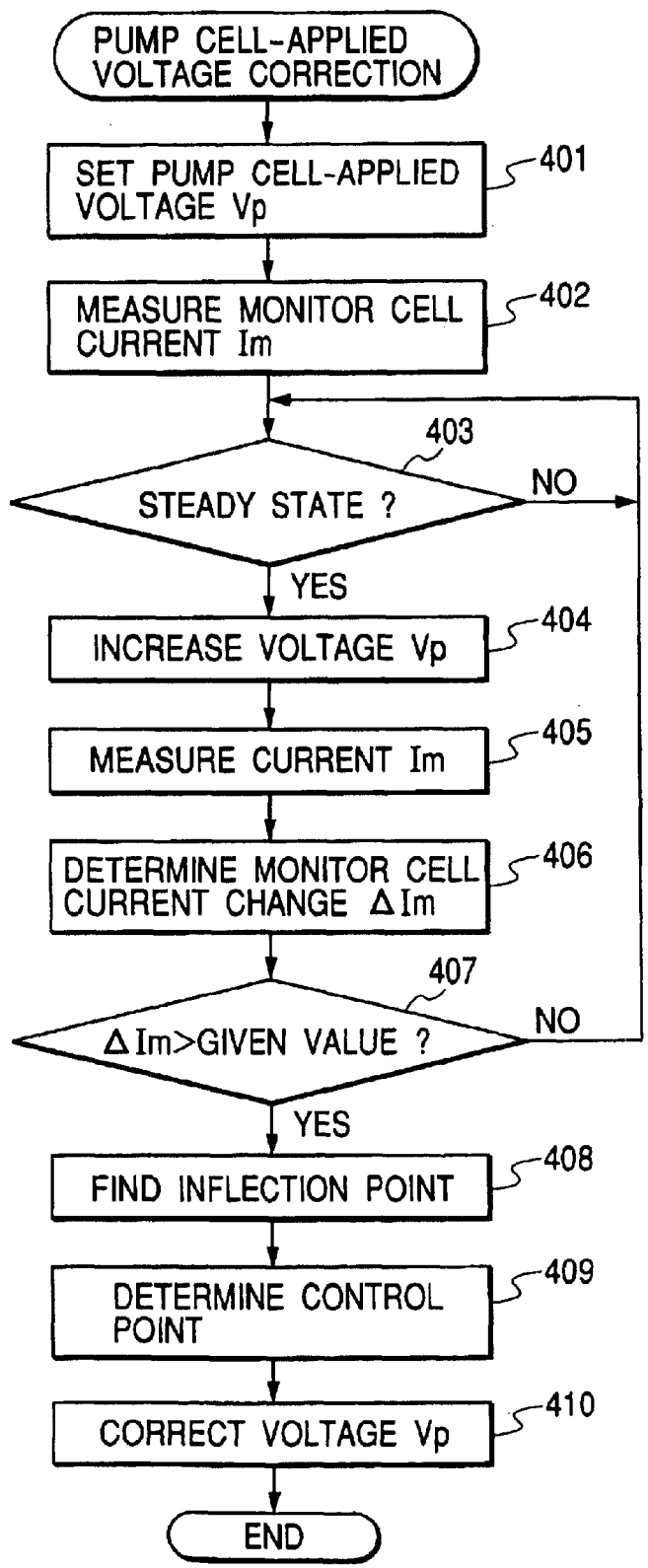
FIG. 12 is a flowchart of a program executed to correct a value of voltage to be applied to a pump cell in the fourth embodiment of the invention.

FIG. 12 is a flowchart of a program executed by the controller 170 to correct the pump cell-applied voltage Vp in this embodiment which is different from the one shown in FIG. 5 only in step 404. Other steps are identical, and explanation thereof in detail will be omitted here.

After an initial value of the pump cell-applied voltage Vp is determined in step 401, the routine proceeds to step 402 wherein the monitor cell current Im produced upon the application of the initial value of the pump cell-applied voltage Vp to the pump cell 110 is measured. After the gas concentration sensor 100 is determined in step 403 to be in the steady state, the routine proceeds to step 404 wherein the pump cell-applied voltage Vp applied to the pump cell 110 is increased by a given value. The routine proceeds to step 405 wherein after converged, the monitor cell current Im is measured.

The routine proceeds to step 406 wherein the value of the monitor cell current Im, as measured in step 406, is subtracted from that one program cycle earlier to determine the monitor cell current change ΔIm. The routine proceeds to step 407 wherein it is determined whether the monitor cell current change ΔIm is less than a predetermined value or not. If a NO answer is obtained meaning that the monitor cell current change ΔIm is lower than the predetermined value, then the routine returns back to step 403 to increase the pump cell-applied voltage Vp by the given value again in step 404 and measure the monitor cell current change ΔIm again in step 406.

If a YES answer is obtained in step 407, then the routine proceeds to step 408 wherein the inflection point A of the monitor cell current Im is located in the manner, as described above, based on the monitor cell current change ΔIm, as determined in step 407 to be smaller than the predetermined value, and a corresponding value of the pump cell-applied voltage Vp is determined.

The routine proceeds to step 409 wherein the given offset value is added to the value of the pump cell-applied voltage Vp at the inflection point A of the monitor cell current Im to determine the control point of the pump cell-applied voltage Vp that is a reference voltage value to which the pump cell-applied voltage Vp is to be controlled. The routine proceeds to step 410 wherein the target applying voltage line LX1 is corrected using the control point as determined in step 409.

The determination of the inflection point A of the monitor cell current Im may alternatively be accomplished using the monitor cell current change ΔIm from the initial value of the monitor cell current Im, as described in the second embodiment, or the monitor cell current change ΔIm determined, as described in the third embodiment, based on the reference current value defined outside the flat range within which the monitor cell current Im hardly changes regardless of a change in the pump cell-applied voltage Vp.

The gas concentration measuring apparatus of the fourth embodiment may alternatively be designed to find the value of the pump cell-applied voltage Vp which corresponds to the inflection point C of the sensor cell current Is, not the monitor cell current Im and determine the control point to which the pump cell-applied voltage Vp is controlled.

The above operation may be achieved by executing the program of FIG. 12 using the sensor cell current Is and a sensor cell current change ΔIs instead of the monitor cell current Im and the monitor cell current change ΔIm. Specifically, an initial value of the pump cell-applied voltage Vp is first determined. The pump cell-applied voltage Vp is then applied to the pump cell 110. A resulting value of the sensor cell current Is is measured. The pump cell-applied voltage Vp applied to the pump cell 110 is increased in a unit of a given level. A resulting value of the sensor cell current Is is measured from which the initial value of the sensor cell current Is is subtracted to determine the sensor cell current change ΔIs. It is determined whether the sensor cell current change ΔIs is smaller than a predetermined value or not. When the sensor cell current change ΔIs becomes smaller than the predetermined value, the inflection point C of the sensor cell current Is is located based on the sensor cell current change ΔIs, as determined to be greater than the predetermined value, and a corresponding value of the pump cell-applied voltage Vp is determined. A given offset value is added to the value of the pump cell-applied voltage Vp at the inflection point C of the sensor cell current Is to determine the control point of the pump cell-applied voltage Vp that is a reference voltage value to which the pump cell-applied voltage Vp is to be controlled. Finally, the target applying voltage line LX1 is corrected using the control point in the same manner as described above.

A gas concentration measuring apparatus of the fifth embodiment will be described below.

The gas concentration measuring apparatus of each of the first to fourth embodiments works to change the pump cell-applied voltage Vp stepwise and measure resulting values of the monitor cell current Im to find the inflection point A. This operation needs to wait convergence of the monitor cell current Im after the change of the pump cell-applied voltage Vp, thus requiring a relatively long period of time to measure the monitor cell current change ΔIm. Specifically, when the pump cell-applied voltage Vp is swept to find the inflection point A, the sensor cell current Is and the monitor cell current Im change greatly in synchronization with each other, which results in a decreased period of time within which the concentration of NOx is to be measured. It is, therefore, essential to minimize the length of time required for correcting the pump cell-applied voltage Vp.

Figure 13:
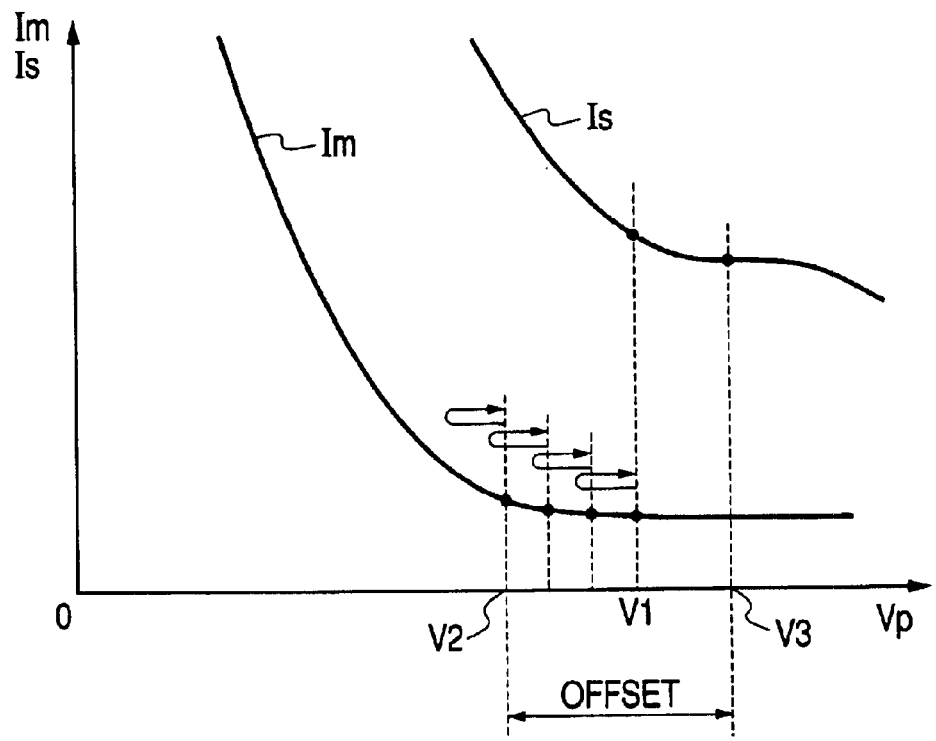
FIG. 13 is a graph which illustrates changes in monitor cell current to be measured when a pump cell-applied voltage is swept sequentially in the fifth embodiment of the invention.

In order to avoid the above problems, the gas concentration measuring apparatus of this embodiment is designed to sweep the pump cell-applied voltage Vp to either of higher and lower voltage sides and measure the waveform of a resulting change in monitor cell current Im to determine the inflection point A. This operation will be described below with reference to FIG. 13.

It is assumed that the pump cell-applied voltage Vp is initially set to a voltage value V1. Subsequently, the pump cell-applied voltage Vp is swept to a lower level temporarily. The waveform of a resulting change in the monitor cell current Im is analyzed to locate the inflection point A. A sweep of the pump cell applied voltage Vp is set greater than a given cyclic voltage change, as described later. The pump cell-applied voltage Vp is swept preferably in a cycle of 200 msec. or less (i.e., 5 Hz or more), and more preferably in a cycle of 100 msec. or less (i.e., 10 Hz or more).

In the shown case, the inflection point A of the monitor cell current Im corresponds to a value V2 of the pump cell-applied voltage Vp. Like the above embodiments, a given offset value is added to the value V2 to define the control point (i.e., the value V3 of the pump cell-applied voltage Vp) that is a target voltage to which the pump cell-applied voltage Vp is corrected.

Figure 14:
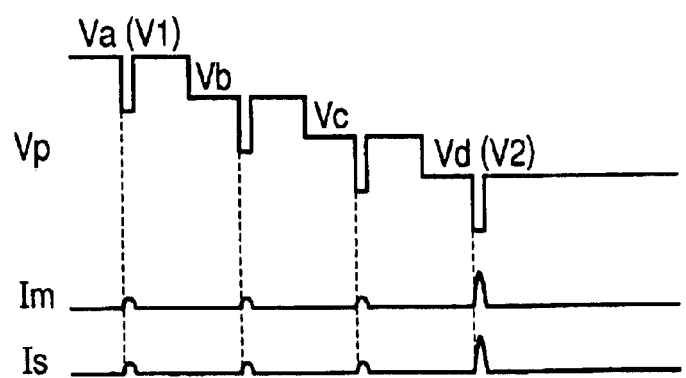
FIG. 14 is a time chart which illustrates changes in monitor cell current and sensor cell current in terms of a change in pump cell-applied voltage in FIG. 13.

FIG. 14 is a time chart which illustrates changes in monitor cell current Im and sensor cell current Is following a change in pump cell-applied voltage Vp.

The pump cell-applied voltage Vp is decreased from Va to Vd cyclically. Each of the values Va to Vd is also swept for a short period of time. Resulting changes appear at the monitor cell current Im and the sensor cell current Is. In the shown case, the changes in monitor cell current Im and sensor cell current Is arising from the sweep of the pump cell-applied voltage Vp from the values Va, Vb, and Vc are smaller, while those arising from the sweep of the pump cell-applied voltage Vp from the value Vd is greater. Specifically, the change in monitor cell current Im in response to the sweep of the change in pump cell-applied voltage Vp becomes great near the inflection point A of the monitor cell current Im. The location of the inflection point A may, therefore, be achieved easily by monitoring the waveform of the change in monitor cell current Im arising from the sweep of the pump cell-applied voltage Vp.

Figure 15:
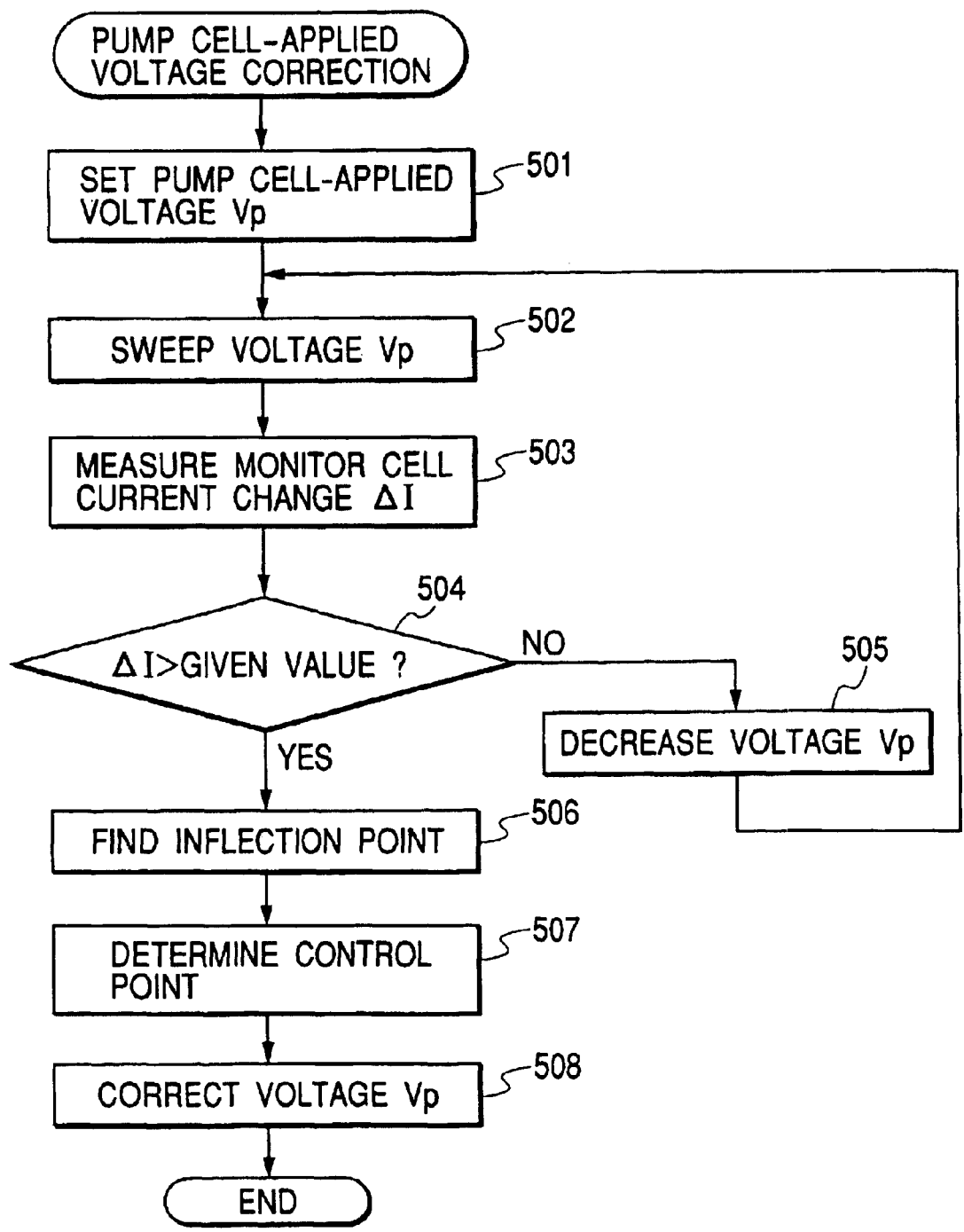
FIG. 15 is a flowchart of a program executed to correct a value of voltage to be applied to a pump cell in the fifth embodiment of the invention.

FIG. 15 is a flowchart of a program executed by the controller 170 to correct the pump cell-applied voltage Vp in the fifth embodiment which is different from the one shown in FIG. 5 in steps 502 to 505.

After entering the program, the routine proceeds to step 501 wherein an initial value of the pump cell-applied voltage Vp is determined and applied to the pump cell 110.

The routine proceeds to step 502 wherein the value of the pump cell-applied voltage Vp as determined in step 501 is swept to a lower level at a given amplitude. The routine proceeds to step 503 wherein a change in monitor cell current ΔI airing from the sweep of the pump cell-applied voltage Vp is measured. The routine proceeds to step 504 wherein the monitor cell current change ΔI is greater than a given value or not. If a NO answer is obtained meaning that the monitor cell current change ΔI is less than or equal to the given value, then the routine proceeds to step 505 wherein the pump cell-applied voltage Vp is decreased by a constant value. The routine returns back to step 502 wherein the value of the pump cell-applied voltage Vp, as provided in step 505, is swept to the lower level at the given amplitude again. Steps 502 to 505 are repeated until the monitor cell current change ΔI is determined in step 504 as being greater than the given value. If such a determination is made, then the routine proceeds to step 506 wherein the inflection point A of the monitor cell current Im is located in the manner as described above. The routine proceeds to step 507 wherein a given offset value is added to the value of the pump cell-applied voltage Vp at the inflection point A of the monitor cell current Im, as determined in step 506, to determine the control point of the pump cell-applied voltage Vp that is a reference voltage value to which the pump cell-applied voltage Vp is to be controlled. The routine proceeds to step 508 wherein the target applying voltage line LX1 is corrected using the control point as determined in step 507.

The gas concentration measuring apparatus of this embodiment eliminates the need for waiting the convergence of the monitor cell current Im following the change in pump cell-applied voltage Vp in order to locate the inflection point A of the monitor cell current Im, thereby resulting in a decrease in time required for correcting the pump cell-applied voltage Vp.

In step 502, the pump cell-applied voltage Vp may alternatively be swept both to the higher and lower voltage sides, thereby facilitating return of the pump cell-applied voltage Vp.

The gas concentration measuring apparatus of the fifth embodiment may alternatively be designed to find the value of the pump cell-applied voltage Vp which corresponds to the inflection point C of the sensor cell current Is, not the monitor cell current Im and determine the control point to which the pump cell-applied voltage Vp is controlled.

The above operation may be achieved by executing the program of FIG. 15 using the sensor cell current Is and a sensor cell current change ΔIs instead of the monitor cell current Im and the monitor cell current change ΔIm. Specifically, an initial value of the pump cell-applied voltage Vp is first determined and applied to the pump cell 110, after which it is swept at a given amplitude. A resulting change in the sensor cell current Is is measured. This measurement is performed each time the pump cell-applied voltage is decreased by the constant value. When the sensor cell current change ΔIs becomes greater than the given value, the inflection point C of the sensor cell current Is is located in the same manner as described above. The given offset value is added to the value of the pump cell-applied voltage Vp at the inflection point C of the sensor cell current Is to determine the control point of the pump cell-applied voltage Vp that is a reference voltage value to which the pump cell-applied voltage Vp is to be controlled. Finally, the target applying voltage line LX1 is corrected using the control point in the same manner as described above.

A gas concentration measuring apparatus of the sixth embodiment will be described below with reference to FIG. 16 which is designed to sweep an initial value of the pump cell-applied voltage Vp cyclically at different amplitudes and measure resulting changes in monitor cell current Im to locate the inflection point A.

Figure 16:
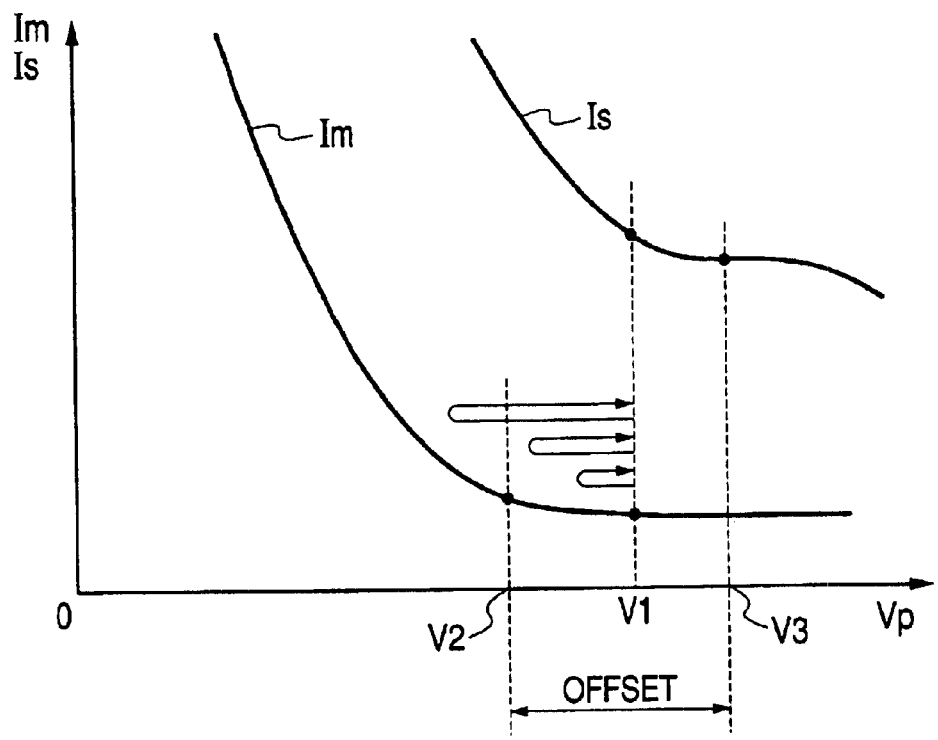
FIG. 16 is a graph which illustrates changes in monitor cell current to be measured when a pump cell-applied voltage is swept sequentially at different amplitudes in the sixth embodiment of the invention.

In FIG. 16, the pump cell-applied voltage Vp is initially set to a voltage value V1. Subsequently, the voltage value V1 is swept in sequence at different amplitudes. Resulting changes in monitor cell current Im are analyzed to locate the inflection point A. The sweep of the pump cell applied voltage Vp is performed preferably in a cycle of 200 msec. or less (i.e., 5 Hz or more), and more preferably in a cycle of 100 msec. or less (i.e., 10 Hz or more).

In the shown case, the inflection point A of the monitor cell current Im corresponds to the value V2 of the pump cell-applied voltage Vp. Like the above embodiments, a given offset value is added to the value V2 to define the control point (i.e., the value V3 of the pump cell-applied voltage Vp) that is a target voltage to which the pump cell-applied voltage Vp is corrected.

Figure 17:
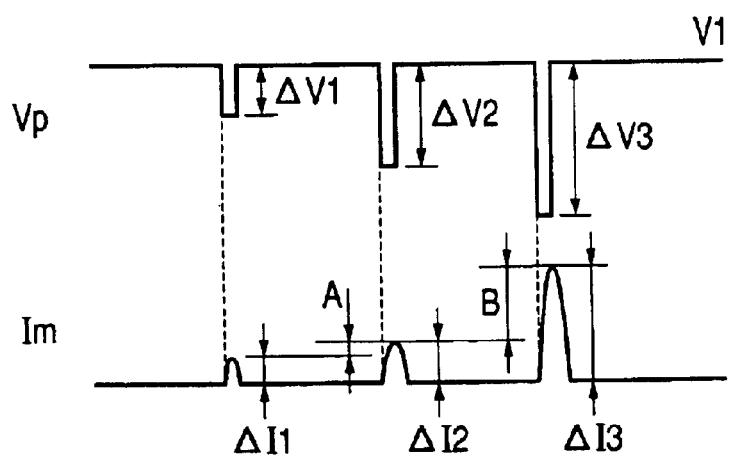
FIG. 17 is a time chart which illustrates changes in monitor cell current and sensor cell current in terms of a change in pump cell-applied voltage in FIG. 16.

FIG. 17 is a time chart which illustrates changes in monitor cell current Im and sensor cell current Is arising from the sweep of the pump cell-applied voltage Vp.

In the shown example, the initial value VI of the pump cell-applied voltage Vp is swept in sequence at three different amplitudes ΔV1, ΔV2, and ΔV3. For instance, the amplitude ΔV2 is twice greater than the amplitude ΔV1. The amplitude ΔV3 is three times greater than the amplitude ΔV1. The sweep of the initial value V1 at the amplitudes ΔV1, ΔV2, and ΔV3 results in changes ΔI1, ΔI2, and ΔI3 in monitor cell current Im which are used in locating the inflection point A of the monitor cell current Im.

Figure 18:
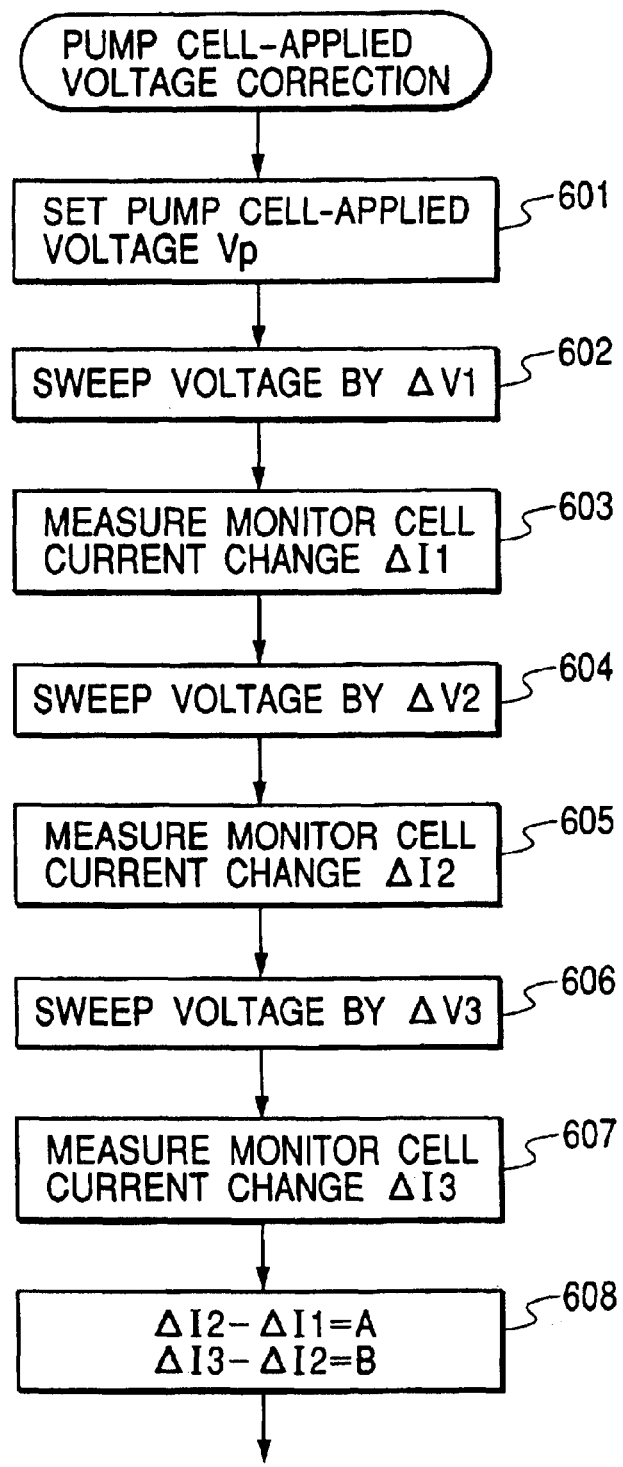
FIGS. 18 and 19 show a flowchart of a program executed to correct a value of voltage to be applied to a pump cell in the sixth embodiment of the invention.
Figure 19:
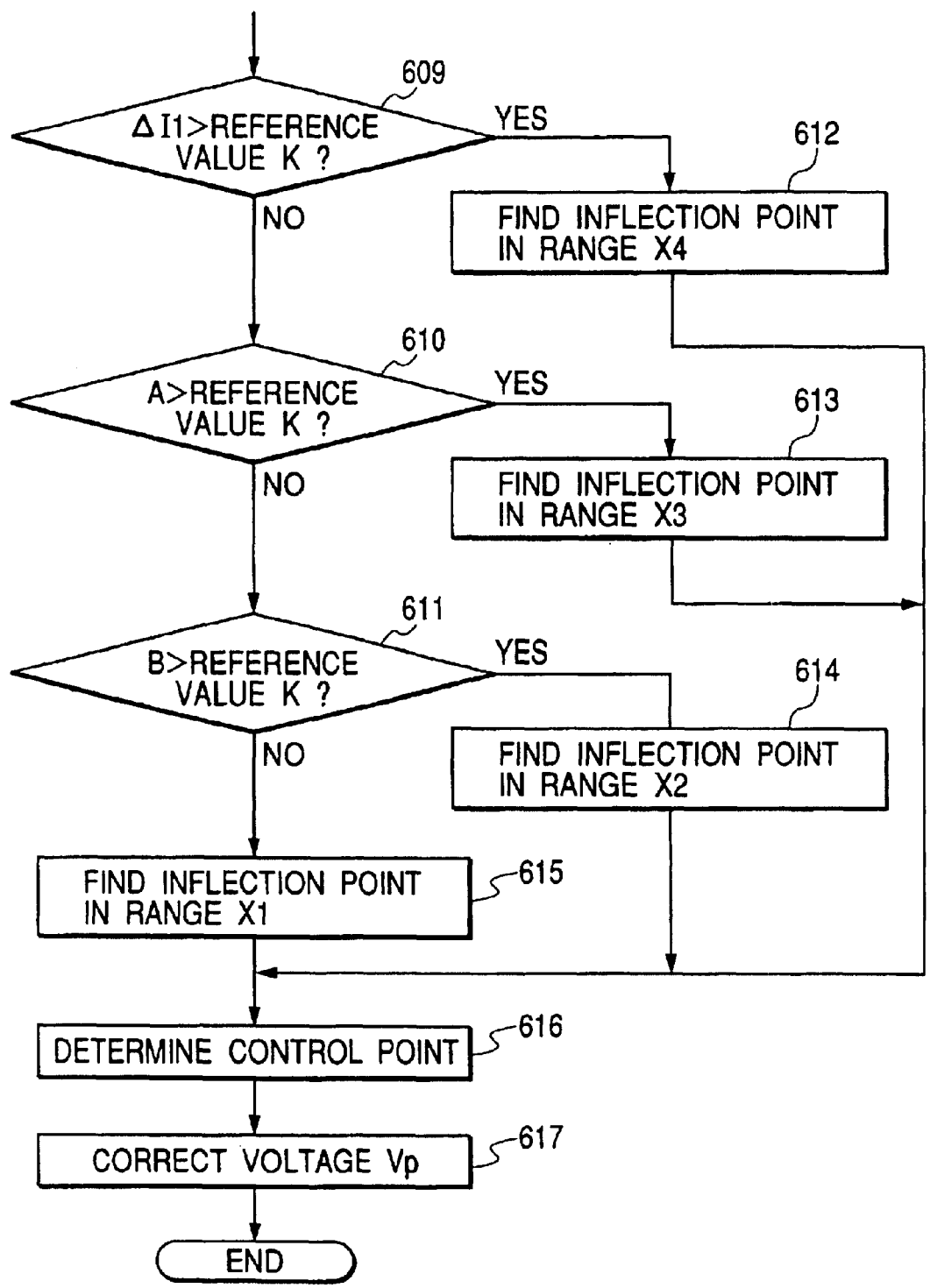

FIGS. 18 and 19 show a program executed by the controller 170 of the sixth embodiment in a cycle of, for example, several seconds to correct the pump cell-applied voltage Vp.

After entering the program, the routine proceeds to step 601 wherein an initial value of the pump cell-applied voltage Vp is determined and applied to the pump cell 110.

The routine proceeds to step 602 wherein the value of the pump cell-applied voltage Vp as determined in step 601 is swept at the first amplitude ΔV1. The routine proceeds to step 603 wherein a change in monitor cell current Im (i.e., the monitor cell current change ΔI1) airing from the sweep of the pump cell-applied voltage Vp is measured. The routine proceeds to step 604 wherein the value of the pump cell-applied voltage Vp as determined in step 601 is swept at the second amplitude ΔV2. The routine proceeds to step 605 wherein the monitor cell current change ΔI2 airing from the sweep of the pump cell-applied voltage Vp in step 604 is measured. The routine proceeds to step 606 wherein the value of the pump cell-applied voltage Vp as determined in step 601 is swept at the third amplitude ΔV3. The routine proceeds to step 607 wherein the monitor cell current change ΔI3 airing from the sweep of the pump cell-applied voltage Vp in step 606 is measured.

The routine proceeds to step 608 wherein differences A and B between the monitor cell current changes ΔI1 and ΔI2 (ΔI2−ΔI1) and between the monitor cell current changes ΔI2 and ΔI3(ΔI3−ΔI2) are determined.

The routine proceeds to step 609 of FIG. 19. Steps 609 to 615 determines the inflection point A of the monitor cell current Im using the monitor cell current change ΔI1 and the differences A and B. The operations in steps 609 to 615 are described below with reference to FIG. 20.

Figure 20:
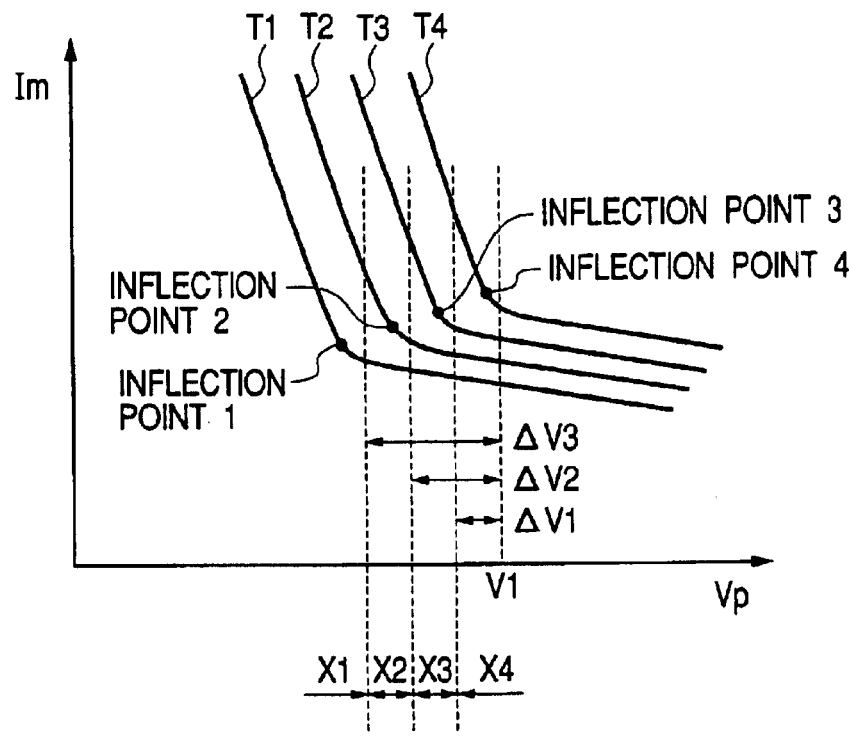
FIG. 20 is a map illustrating shifts in pump cell applied voltage-to-monitor cell current characteristic resulting from aging of a gas concentration sensor which is used in an operation, as shown in FIGS. 18 and 19.

FIG. 20 illustrates examples wherein the Vp-Im curve is shifted from T1 to T2, T3, and T4 due to the aging of the gas concentration sensor 100, thereby resulting in shift in inflection point A of the monitor cell current Im from 1 to 2, 3, and 4. V1 indicates an initial value of the pump cell-applied voltage Vp.

X1, X2, X3, and X4 indicate voltage ranges of the pump cell-applied voltage Vp used to locate the inflection point A of the monitor cell current Im. The voltage range X1 is defined below a value of V1−ΔV3. The voltage range X2 is defined between the value of V1−ΔV3 and a value of V1−ΔV2. The voltage range X3 is defined between the value of V1−ΔV2 and a value of V1−ΔV1. The voltage range is defined above a value of V1−ΔV1.

In step 609, it is determined whether the monitor cell current change ΔI1 airing from the sweep of the pump cell-applied voltage Vp at the first amplitude ΔV1 is greater than a given reference value K or not. If a NO answer is obtained, then the routine proceeds to step 610 wherein the difference A is greater than the reference value K or not. If a NO answer is obtained, then the routine proceeds to step 611 wherein it is determined whether the difference B is greater than the reference value K or not.

If the Vp-Im curve of the monitor cell current Im is the one labeled T4, the monitor cell current change ΔI1 airing from the sweep of the pump cell-applied voltage Vp at the first amplitude ΔV1 exceeds the reference value K. A YES answer is, thus, obtained in step 609. The routine proceeds to step 612 wherein the point 4 on the Vp-Im curve T4, as shown in FIG. 20, is defined as the inflection point A of the monitor cell current Im.

If the Vp-Im curve of the monitor cell current Im is the one labeled T3, it will cause the difference A(=ΔI2−ΔI1) to exceed the reference value K. A YES answer is, thus, obtained in step 610. The routine proceeds to step 613 wherein the point 3 on the Vp-Im curve T3 is defined as the inflection point A of the monitor cell current Im.

If the Vp-Im curve of the monitor cell current Im is the one labeled T2, it will cause the difference B(=ΔI3−ΔI2) to exceed the reference value K. A YES answer is, thus, obtained in step 611. The routine proceeds to step 614 wherein the point 2 on the Vp-Im curve T2 is defined as the inflection point A of the monitor cell current Im.

If the Vp-Im curve of the monitor cell current Im is the one labeled T1, NO answers are all obtained in steps 609 to 611. The routine, thus, proceeds to step 615 wherein the point 1 on the Vp-Im curve T1 is defined as the inflection point A of the monitor cell current Im.

After the inflection point A of the monitor cell current Im is determined in step 612, 613, 614, or 615, the routine proceeds to step 616 wherein a given offset value is added to the value of the pump cell-applied voltage Vp at the inflection point A of the monitor cell current Im to determine the control point of the pump cell-applied voltage Vp that is a reference voltage value to which the pump cell-applied voltage Vp is to be controlled. The routine proceeds to step 617 wherein the target applying voltage line LX1 is corrected using the control point as determined in step 507.

The sweep of the pump cell-applied voltage Vp may alternatively be performed cyclically at a single amplitude or two or more than three different amplitudes to locate the inflection point A of the monitor cell current Im. The sweep may also be performed to a higher voltage side. Another algorithm may be used to locate the inflection point A using a change in monitor cell current Im.

Figure 21:
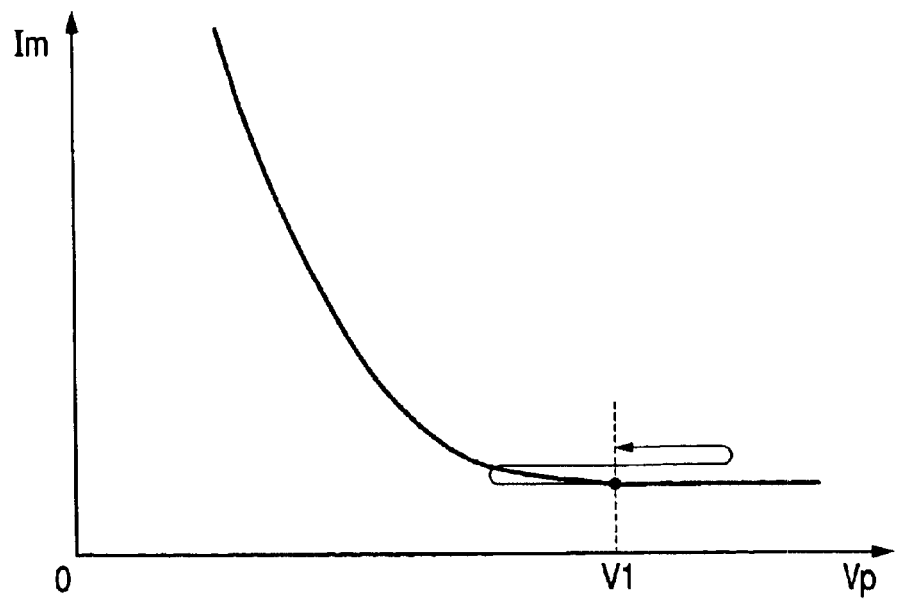
FIG. 21 illustrates a sweep of a pump cell-applied voltage for determining an inflection point of a pump cell applied voltage-to-monitor cell current curve which is performed in the sixth embodiment.

The gas concentration measuring apparatus of this embodiment may alternatively be designed to sweep the pump cell-applied voltage Vp, as shown in FIG. 21, both to higher and lower voltage sides and measure resulting changes in monitor cell current Im to locate the inflection point A of the monitor cell current Im. The sweep of the pump cell-applied voltage Vp from V1 both to the higher and lower voltage sides causes the monitor cell current Im to change at an amplitude that is a function of the distance between the voltage value V1 and the inflection point A of the monitor cell current Im.

Figure 22A:
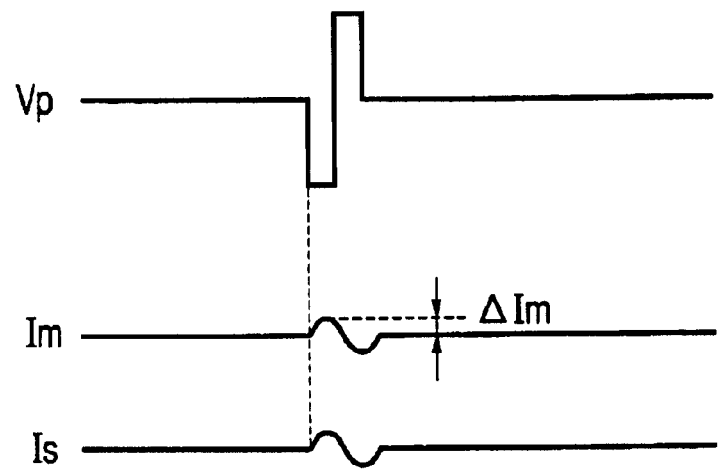
FIG. 22(a) shows changes in current outputs of a monitor cell and a sensor cell arising from a sweep of voltage applied to a pump cell when the voltage applied to the pump cell lies away from an inflection point of a monitor cell current.
Figure 22B:
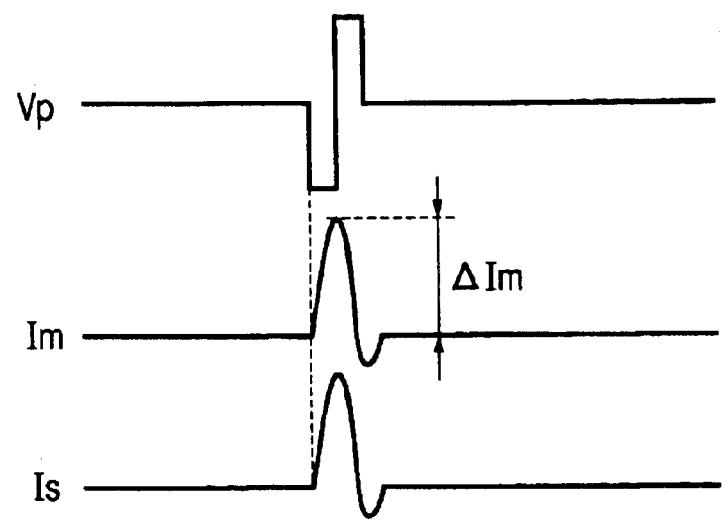
FIG. 22(b) shows changes in current outputs of a monitor cell and a sensor cell arising from a sweep of voltage applied to a pump cell when the voltage applied to the pump cell is close to an inflection point of a monitor cell current.

For example, if the inflection point A is not close to the voltage value V1, the sweep of the pump cell-applied voltage Vp result in, as shown in FIG. 22(*a*), small changes in the monitor cell current Im and the sensor cell current Is which is substantially equal in magnitude to each other. In this case, the controller 170 may decide that the inflection point A has not been shifted from one found in a previous cycle, so that a corresponding value of the pump cell-applied voltage Vp remains unchanged and that a target value of the pump cell-applied voltage Vp to be applied to the pump cell 110 needs not be corrected and output it directly to the pump cell 110.

Alternatively, if the inflection point A is close to the voltage value V1, it results in, as shown in FIG. 22(*b*), great differences between the changes in monitor cell current Im and sensor cell current Is rising from the sweep of the pump cell-applied voltage Vp to the higher voltage side and to the lower voltage side. Specifically, if the change in monitor cell current Im or sensor cell current Is to one of higher and lower sides is different from that to the other side greatly, the controller 170 may conclude that the inflection point A has been changed. In the shown case, the controller 170 may conclude that the inflection point A has been shifted in a direction (i.e., the right direction in FIG. 21) opposite a direction of a change in pump cell-applied voltage Vp leading to a greater change in monitor cell current Im and that the pump cell-applied voltage Vp should be corrected.

The gas concentration measuring apparatus of the sixth embodiment may alternatively be designed to find the value of the pump cell-applied voltage Vp which corresponds to the inflection point C of the sensor cell current Is, not the monitor cell current Im and determine the control point to which the pump cell-applied voltage Vp is controlled.

The above operation may be achieved by executing the program shown in FIGS. 18 and 19 using the sensor cell current change ΔIs instead of the monitor cell current change ΔIm. Specifically, an initial value of the pump cell-applied voltage Vp is first determined and applied to the pump cell 110, after which it is swept in sequence at the amplitudes ΔV1, ΔV2, and ΔV3. Resulting changes in the sensor cell current Is are measured to locate the inflection point C of the sensor cell current Is in the same manner as described above with reference to FIG. 20. The given offset value is added to the value of the pump cell-applied voltage Vp at the inflection point C of the sensor cell current Is to determine the control point of the pump cell-applied voltage Vp that is a reference voltage value to which the pump cell-applied voltage Vp is to be controlled. Finally, the target applying voltage line LX1 is corrected using the control point in the same manner as described above.

The sweep of the pump cell-applied voltage Vp may be performed, as shown in FIG. 21, from the voltage value V1 both to the higher and lower voltage sides to locate the inflection point C of the sensor cell current Is. If, like the monitor cell current Im, the inflection point C is close to the voltage value V1, it will cause a change in sensor cell current Is to one of higher and lower voltage sides to be different from that to the other side greatly. The controller 170 may decide that the inflection point C has been changed undesiraably.

A gas concentration measuring apparatus of the seventh embodiment will be described below which is designed to change the pump cell-applied voltage Vp stepwise to one of higher and lower voltage sides to find a first pump cell-applied voltage corresponding to the inflection point A of the monitor cell current Im and also change the pump cell-applied voltage Vp stepwise to the other side to find a second pump cell-applied voltage corresponding to the value of the monitor cell current kept almost constant and define it as the control point to which the pump cell-applied voltage Vp is controlled.

Figure 23A:
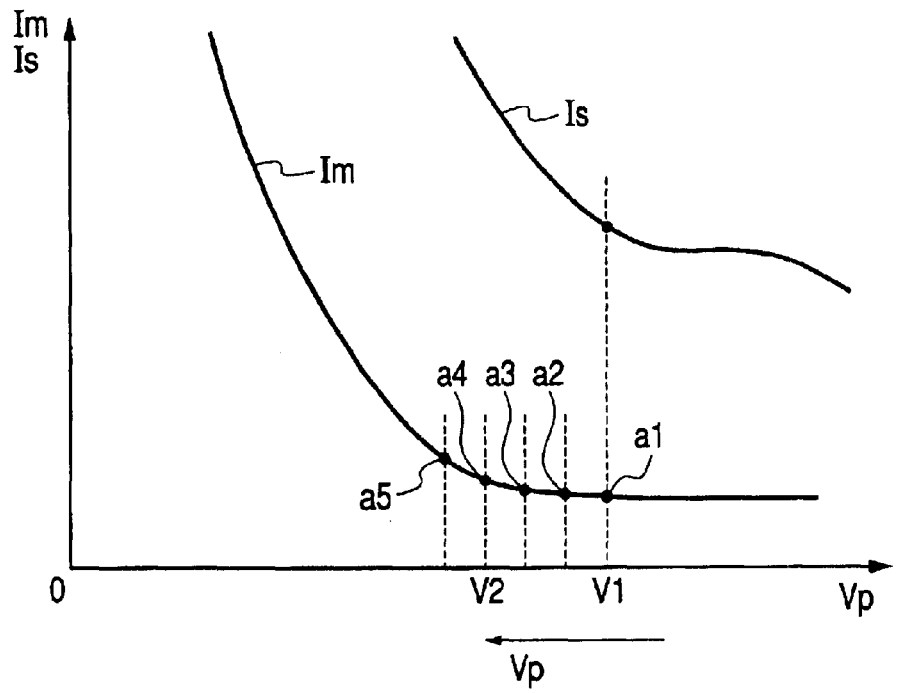
FIGS. 23(a) and 23(b) show changes in monitor cell current to be measured when a pump cell-applied voltage changes stepwise to a higher and a lower voltage side in the seventh embodiment of the invention.
Figure 23B:
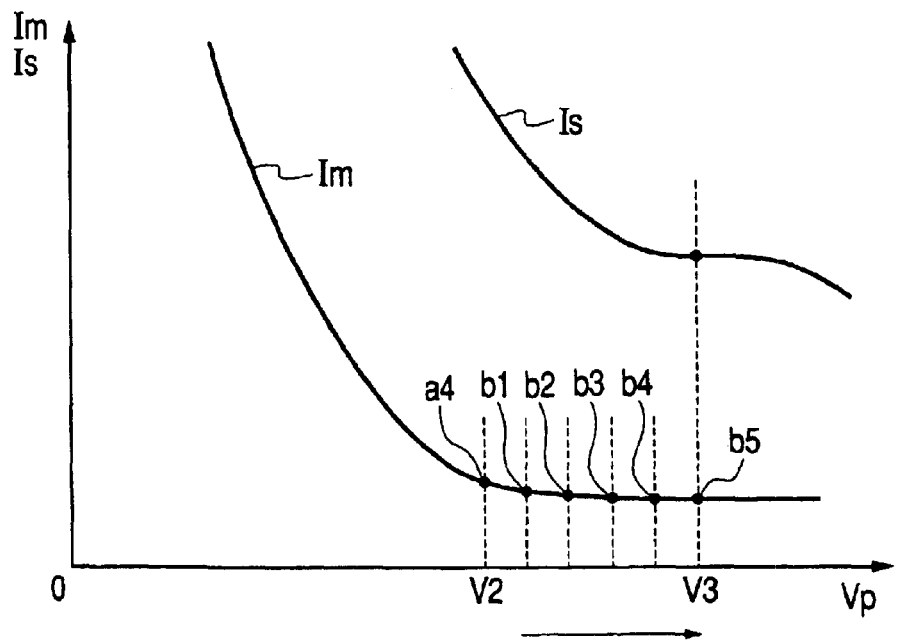

FIG. 23(a) illustrates stepwise changes of the pump cell-applied voltage Vp to the lower voltage side to find the first pump cell-applied voltage. FIG. 23(b) illustrates stepwise changes of the pump cell-applied voltage Vp to the higher voltage side to find the second pump cell-applied voltage.

In FIG. 23(a), the pump cell-applied voltage Vp is initially set to a voltage value V1. The monitor cell current Im is measured at a point a1. Subsequently, the pump cell-applied voltage Vp is decreased in a unit of a preselected voltage level cyclically. Resulting values of the monitor cell current Im are measured at points a2, a3, a4, and a5 and used to find the inflection point A of the monitor cell current Im. In the shown example, the point a4 immediately preceding the point a5 is defined as the inflection point A.

After the inflection point A is found, the pump cell-applied voltage Vp is, as shown in FIG. 23(b), increased from the voltage value V2 at the inflection point A in a unit of a preselected voltage level cyclically. Resulting values of the monitor cell current Im are measured at points b1, b2, b3, b4, and b5 and used to find the control point to which the pump cell-applied voltage Vp is controlled. In the shown example, the voltage value V3 at the point b5 is defined as the control point.

Figure 24:
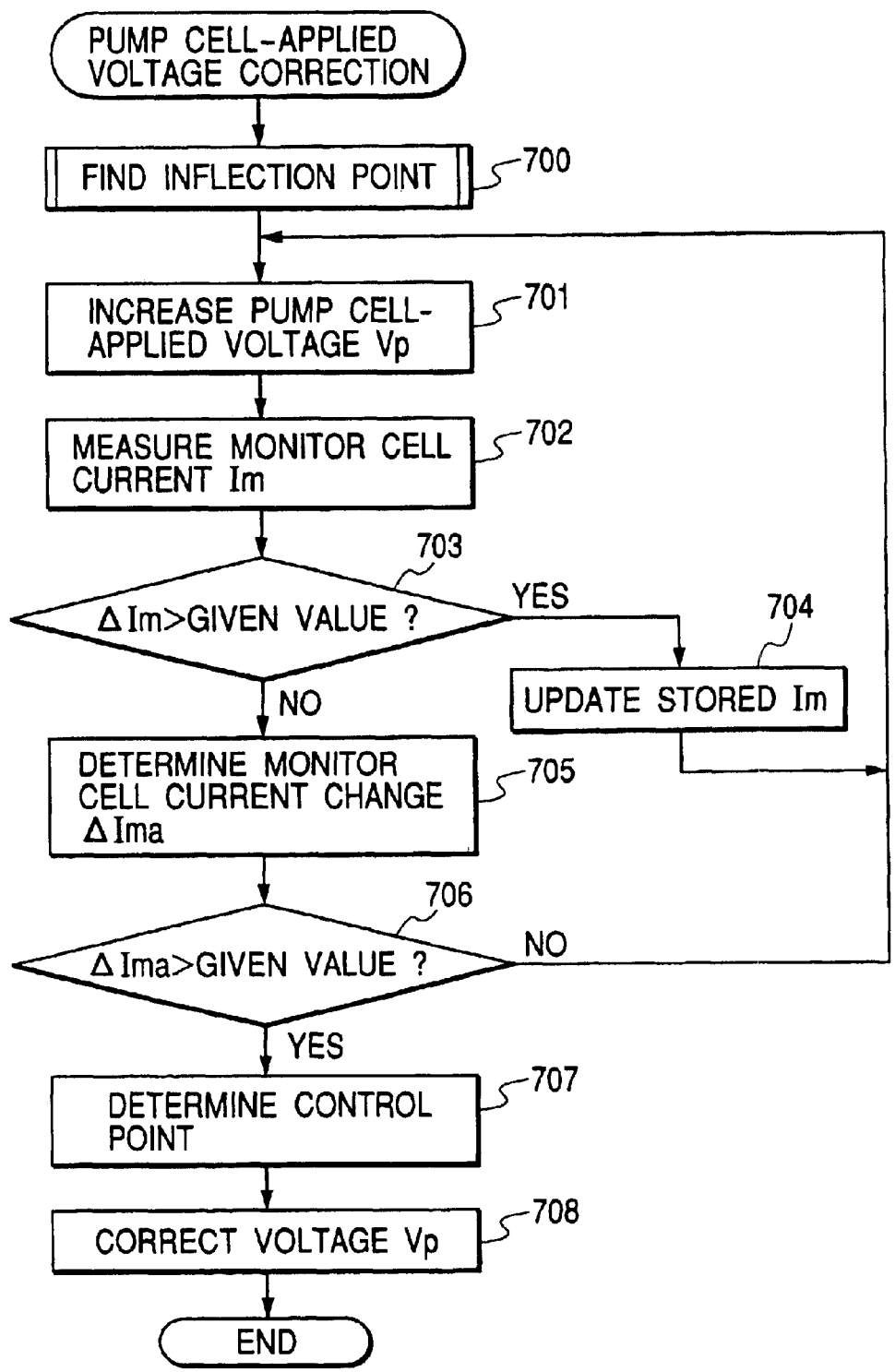
FIG. 24 is a flowchart of a program executed to correct a value of voltage to be applied to a pump cell in the seventh embodiment of the invention.

FIG. 24 is a flowchart of a program executed by the controller 170 to correct the pump cell-applied voltage Vp in this embodiment.

After entering the program, the routine proceeds to step 700 wherein the inflection point A is found, and the value of the monitor cell current Im is stored in the memory of the controller 170. This operation may be achieved using a sequence of steps 101 to 108 of FIG. 5, steps 201 to 208 of FIG. 8, steps 301 to 310 of FIG. 10, steps 501 to 506 of FIG. 15, or steps 601 to 615 of FIGS. 18 and 19.

Subsequently, the routine proceeds to step 701 wherein the pump cell-applied voltage Vp is increased, as described above, by the preselected voltage level. The routine proceeds to step 702 wherein after converged, the monitor cell current Im is measured. The routine proceeds to step 703 wherein it is determined whether the rate of a change ΔIm in monitor cell current Im arising from the increasing of the pump cell-applied voltage Vp is almost constant or not. For instance, it is determined whether the monitor cell current change ΔIm is greater than 10% of the value of the monitor cell current Im before changed or not. If a YES answer is obtained, then the routine proceeds to step 704 wherein the value of the monitor cell current Im stored in the memory is updated to that as measured in step 702. The routine returns back to step 701 to increase the pump cell-applied voltage Vp by the preselected voltage level again.

Alternatively, if a NO answer is obtained in step 703 meaning that the monitor cell current Im is almost constant in level, then the routine proceeds to step 705 wherein the value of the monitor cell current Im, as measured in step 702, is subtracted from that stored in the memory to determine the monitor cell current change ΔIma. The routine proceeds to step 706 wherein the monitor cell current change ΔIma is less than a given value or not. If a NO answer is obtained, then the routine returns back to step 701. Alternatively, if a YES answer is obtained, then the routine proceeds to step 707 wherein the value of the pump cell-applied voltage Vp provided in this program cycle is defined as the control point. The routine proceeds to step 708 wherein the target applying voltage line LX1 is corrected using the control point as determined in step 707. This enables the sensor cell current Is to be measured within the flat range of the Vp-Is curve, thereby keeping the accuracy of measuring the concentration of NOx.

The first pump cell-applied voltage (i.e., the inflection point A of the monitor cell current Im) may be found by decreasing the pump cell-applied voltage Vp at a greater amplitude, while the second pump cell-applied voltage (i.e., the control point) may be found by increasing the pump cell-applied voltage Vp at a smaller amplitude. This enables the inflection point A of the monitor cell current Im to be determined quickly while keeping the accuracy of finding the control point.

The gas concentration measuring apparatus of this embodiment may alternatively be designed to find the control point using the inflection point C of the sensor cell current Is.

The above operation may be achieved by executing the program of FIG. 24 using the sensor cell current Is and a sensor cell current change ΔIsa instead of the monitor cell current Im and the monitor cell current change ΔIma. Specifically, the inflection point C of the sensor cell current Is is found in the same manner as described above. The value of the sensor cell current Is at the inflection point C is determined and stored in the memory. Subsequently, the pump cell-applied voltage is increased cyclically in the unit of the preselected voltage level. The value of the sensor cell current Is is updated cyclically until the flat range of the Vp-Is curve of the sensor cell current Is is entered. The sensor cell current change ΔIsa is determined by subtracting the latest value of the sensor cell current Is from that stored in the memory. When the sensor cell current change ΔIsa becomes smaller than the given value, an instant value of the pump cell-applied voltage Vp is determined as the control point. Finally, the target applying voltage line LX1 is corrected using the control point in the same manner as described above. This also keeps the accuracy of measuring the concentration of NOx using the sensor cell current Is.

The inflection point C of the sensor cell current Is may be found by decreasing the pump cell-applied voltage Vp at a greater amplitude, while the control point may be found by increasing the pump cell-applied voltage Vp at a smaller amplitude. This enables the inflection point C of the sensor cell current Is to be determined quickly while keeping the accuracy of finding the control point.

A gas concentration measuring apparatus of the eighth embodiment will be described below which is designed to determine the degree of deterioration of the gas concentration sensor 100 based on the inflection point A of the monitor cell current Im.

Figure 25A:
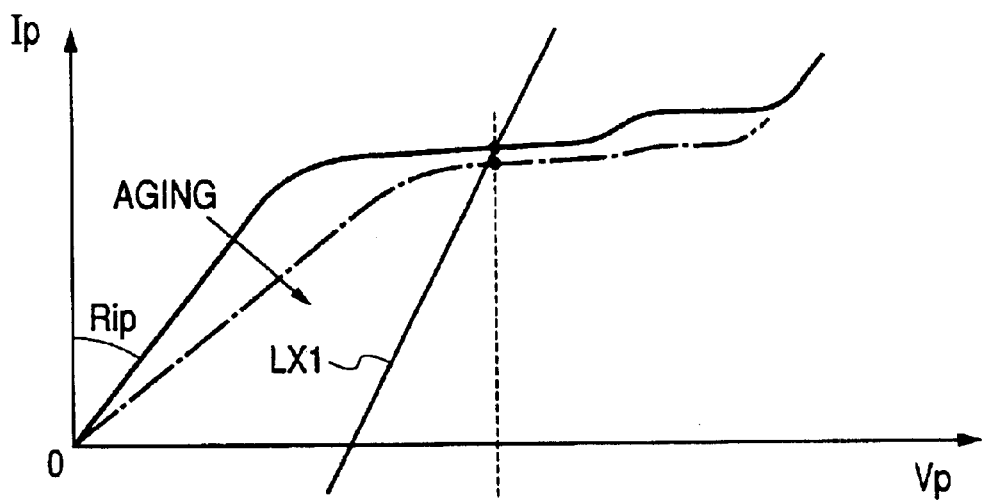
FIG. 25(a) is a graph which shows a relation between a current output of a pump cell and a value of voltage to be applied to the pump cell which is shifted due to, for example, aging of a gas concentration sensor.
Figure 25B:
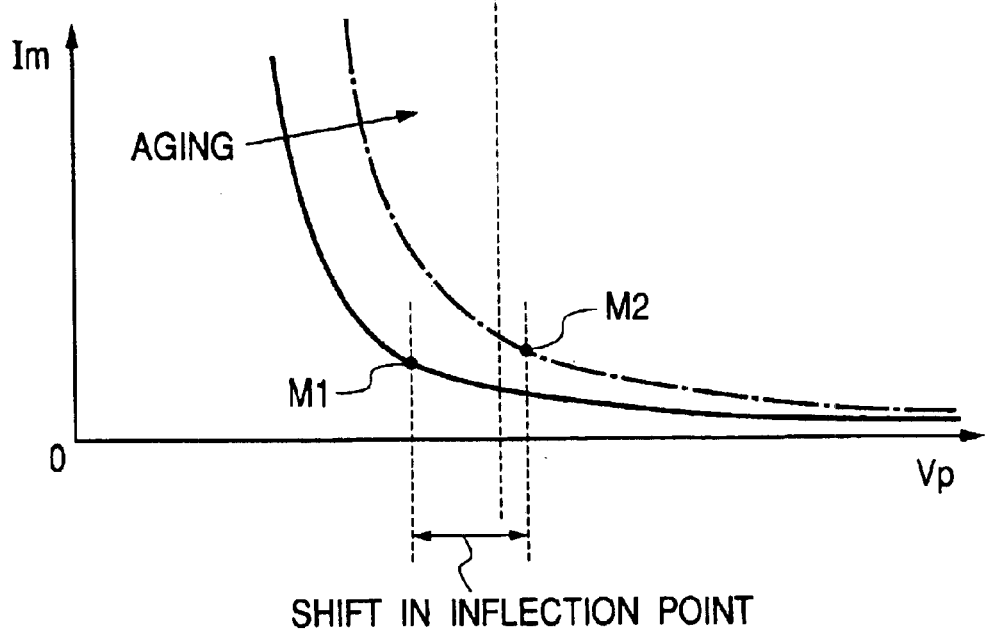
FIG. 25(b) is a graph which shows a shift in current output of a monitor cell current airing from aging of a gas concentration sensor.

Usually, the aging or deterioration of the gas concentration sensor 100 results in a shift in the inflection point A of the monitor cell current Im. The more the deterioration, the more the shift in the inflection point A. Specifically, the inflection point A of the monitor cell current Im is shifted to a higher voltage side of the pump cell-applied voltage Vp as the deterioration of the gas concentration sensor 100 increases. For instance, the inflection point A of the monitor cell current Im is, as illustrated in FIG. 25(b), shifted from M1 to M2 as the deterioration of the gas concentration sensor 100 increases.

The controller 170 works to change the pump cell-applied voltage Vp stepwise or sweep it temporarily in the manner as described above to determine a shift in the inflection point A and determine the degree of deterioration of the gas concentration sensor 100 as a function of the shift in the inflection point A. For instance, when the shift in the inflection point A exceeds a predetermined value, the controller may decide that the degree of the deterioration has increased out of an allowable range and output an alarm signal indicative thereof.

Figure 26A:
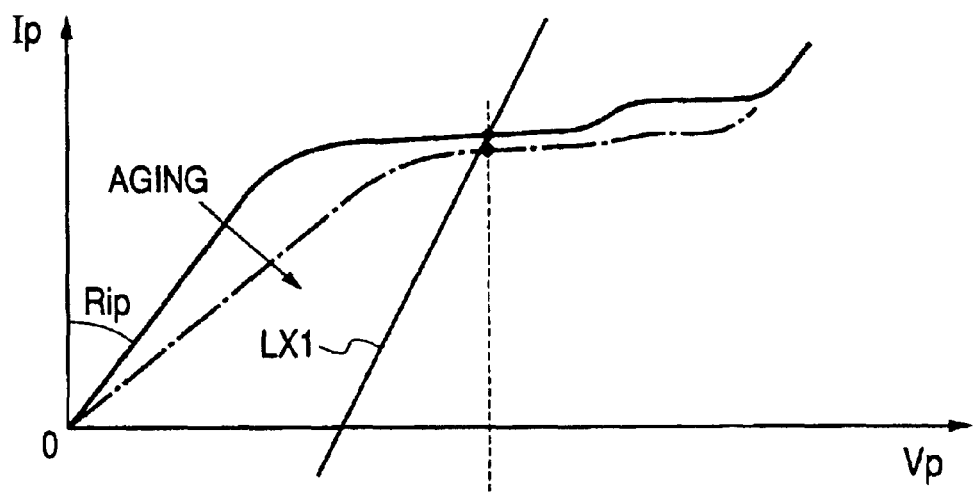
FIG. 26(a) is a graph which shows a relation between a current output of a pump cell and a value of voltage to be applied to the pump cell which is shifted due to, for example, aging of a gas concentration sensor.
Figure 26B:
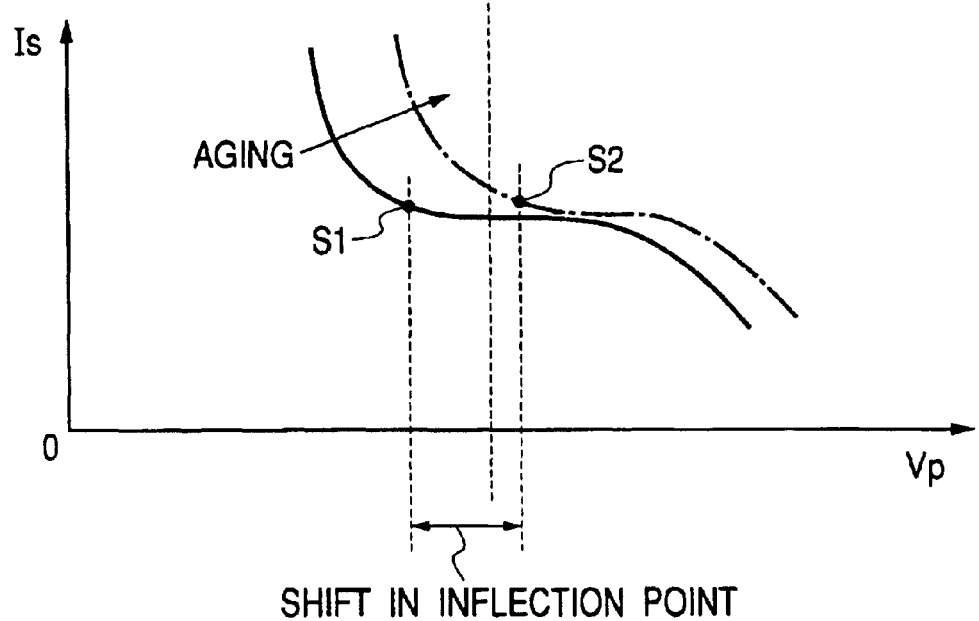
FIG. 26(b) is a graph which shows a shift in current output of a sensor cell current airing from aging of a gas concentration sensor.

The degree of deterioration of the gas concentration sensor 100 may alternatively be determined using a shift in the inflection point C of the sensor cell current Is instead of that of the monitor cell current Im. This is based on the fact that the inflection point C of the sensor cell current Is is shifted, as shown in FIG. 26(b), to the higher voltage side of the pump cell-applied voltage Vp, from S1 to S2 as the deterioration of the gas concentration sensor 100 increases. The controller 170 determines a shift in the inflection point C and determine the degree of deterioration of the gas concentration sensor 100 as a function of the shift in the inflection point C in the same manner as described above. For instance, when the shift in the inflection point C exceeds a predetermined value, the controller may decide that the degree of the deterioration has increased out of an allowable range and output an alarm signal indicative thereof.

The gas concentration measuring apparatus of this embodiment may be designed only to determine the deterioration of the gas concentration sensor 100 without functioning to correct the pump cell-applied voltage Vp using the monitor cell current Im or the sensor cell current Is.

In the above embodiments, the inflection point A or C may be found by changing the pump cell-applied voltage Vp at amplitudes which are decreased stepwise. This increases the accuracy of finding the inflection points A or C.

The inflection point A of the monitor cell current Im may appear within the flange range of the Vp-Ip curve of the sensor cell current Is depending upon the structure of a gas concentration sensor. In this case, the value of the pump cell-applied voltage Vp at the inflection point A may be defined as the control point to which the pump cell-applied voltage Vp is controlled.

In the above embodiments, the controller 170 may work to determine whether the pump cell-applied voltage Vp should be corrected or not immediately before the pump cell-applied voltage Vp is changed at a given amplitude. For instance, the controller 170 may first sweep the initial value of the pump cell-applied voltage Vp temporarily to at least one of higher and lower voltage sides and monitor a resulting waveform of the monitor cell current Im or the sensor cell current Is. If a shift in the inflection point A or the inflection point C arising from the unit-to-unit difference or aging of the gas concentration sensor 100 is observed, it may be determined that the pump cell-applied voltage Vp should be corrected. This enables the correction of the pump cell-applied voltage Vp to be performed only as needed.

There are practically, as shown in FIG. 2(b), two inflection points of the sensor cell current Is across the flat range of the Vp-Is curve. The controller 170 may correct the pump cell-applied voltage Vp using the inflection point on the higher voltage side as well as that on the lower voltage side. In this case, the controller 170 may also use in correcting the pump cell-applied voltage Vp the fact that the sweep of the pump cell-applied voltage Vp to at least one of higher and lower voltage sides will result in a great change in waveform of the monitor cell current Im or the sensor cell current Is when the pump cell-applied voltage Vp is brought close to the inflection point thereof.

In the above embodiments, the initial value of the pump cell-applied voltage Vp is determined by look-up using the target applying voltage line LX1, but however, it may be fixed or determined stepwise as a function of the concentration of oxygen.

The correction of the pump cell-applied voltage Vp and/or the determination of the deterioration of the gas concentration sensor 100 may be made only at startup or rest of the engine. In this case, these operations are performed without interrupting the measurement of the concentration of gasses.

The gas concentration measuring apparatus in each of the above described embodiments may also be used with a multi-cell gas concentration sensor having more than three cells. For example, a gas concentration sensor equipped with two pump cells may be used.

A gas concentration sensor which is designed to decompose and discharge $O_2$ contained in gasses to be measured through a pump cell and decompose HC or CO contained in the gasses after the decomposition of $O_2$ through a sensor cell may be used in each of the above embodiments. Further, the gas concentration measuring apparatus in each of the above embodiments may also be used for measuring the concentration of gasses other than exhaust gasses of an automotive engine.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas concentration measuring apparatus comprising:
a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current as a function of a concentration of a specified gas component contained in the gasses having passed through the pump cell, and a monitor cell working to produce a monitor cell current indicative of a concentration of residual oxygen molecules within the gas chamber, the sensor cell having a given pump cell applied voltage-to-sensor cell current characteristic in which the sensor cell current changes as a function of a pump cell-applied voltage applied to the pump cell; and
a controller working to determine a value of the pump cell-applied voltage when a value of the sensor cell current changes at a given rate in the pump cell applied voltage-to-sensor cell current characteristic, said controller also determining a control point to which the voltage applied to the pump cell is to be controlled using the value of the pump cell-applied voltage.

2. A gas concentration measuring apparatus as set forth in claim 1, wherein said controller changes the voltage applied to the pump cell stepwise cyclically at given amplitudes to one of higher and lower voltage sides and measures a resulting value of the sensor cell current to determine the value of the pump cell-applied voltage when the value of the sensor cell current changes at the given rate in the pump cell applied voltage-to-sensor cell current characteristic.

3. A gas concentration measuring apparatus as set forth in claim 2, further comprising a pump cell-applied voltage determining circuit which looks up a predetermined voltage-to-current relation and determines an initial value of the voltage to be applied to said pump cell as a function of an instant value of the pump cell current produced by said pump cell, and wherein said controller changes the initial value stepwise cyclically to the one of higher and lower voltage sides and measures the resulting value of the sensor cell current to determine the value of the pump cell-applied voltage when the value of the sensor cell current changes at the given rate in the pump cell applied voltage-to-sensor cell current characteristic.

4. A gas concentration measuring apparatus as set forth in claim 2, wherein said given amplitudes at which the voltage applied to the pump cell are changed are constant.

5. A gas concentration measuring apparatus as set forth in claim 2, wherein said given amplitudes at which the voltage applied to the pump cell are changed are decreased in sequence.

6. A gas concentration measuring apparatus as set forth in claim 1, wherein said controller determines the value of the pump cell-applied voltage when the value of the sensor cell current changes at the given rate as the control point.

7. A gas concentration measuring apparatus as set forth in claim 1, wherein said controller adds a given offset value to the value of the pump cell-applied voltage when the value of the sensor cell current changes at the given rate and defines the value to which the offset value is added as the control point.

8. A gas concentration measuring apparatus as set forth in claim 1, wherein said controller changes the voltage applied to the pump cell to determine a fist pump cell-applied voltage at which the value of the sensor cell current changes at the given rate and further changes the voltage applied to the pump cell to determine a second pump cell-applied voltage at which the sensor cell current becomes constant in level, said controller defining the second pump cell voltage as the control point of the voltage to be applied to the pump cell.

9. A gas concentration measuring apparatus as set forth in claim 8, wherein said controller changes the voltage applied to the pump cell stepwise cyclically at given amplitudes in a first voltage level direction to determine the first pump cell-applied voltage and then changes the voltage applied to the pump cell stepwise cyclically at given amplitudes in a second voltage level direction opposite the first voltage level direction to determine the second pump cell-applied voltage.

10. A gas concentration measuring apparatus as set forth in claim 9, wherein the amplitudes at which the voltage applied to the pump cell is changed to determine the first pump cell-applied voltage are greater than those at which the voltage applied to the pump cell is changed to determine the second pump cell-applied voltage.

11. A gas concentration measuring apparatus as set forth in claim 2, wherein said controller compares between values of the sensor cell current produced before and after the voltage applied to the pump cell is changed in each cycle to determine the value of the pump cell-applied voltage when the value of the sensor cell current changes at the given rate.

12. A gas concentration measuring apparatus as set forth in claim 2, wherein said controller defines a value of the sensor cell current corresponding to an initial value of the voltage applied to the pump cell as a reference value and measures a change in the sensor cell current from the reference value in each cycle for use in determining the value of the value of the pump cell-applied voltage when the value of the sensor cell current changes at the given rate.

13. A gas concentration measuring apparatus as set forth in claim 2, wherein said controller defines a value of the sensor cell current produced outside a flat range within which the sensor cell current is kept substantially constant as a reference value and measures a change in the sensor cell current from the reference value in each cycle for use in determining the value of the value of the pump cell-applied voltage when the value of the sensor cell current changes at the given rate.

14. A gas concentration measuring apparatus as set forth in claim 1, wherein said controller sweeps the voltage applied to the pump cell to one of the higher and lower voltage sides in each cycle in which the voltage is changed stepwise and monitors a resulting waveform of the sensor cell current to determine the value of the pump cell-applied voltage when the value of the sensor cell current changes at the given rate.

15. A gas concentration measuring apparatus as set forth in claim 1, wherein said controller sweeps the voltage applied to the pump cell to at least one of the higher and lower voltage sides when starting to determine the value of the pump cell-applied voltage when the value of the sensor cell current changes at the given rate and measures a resultant waveform of the sensor cell current to determine whether the voltage to be applied to the pump cell should be controlled or not.

16. A gas concentration measuring apparatus as set forth in claim 1, wherein said controller sweeps the voltage applied to the pump cell to at least one of the higher and lower voltage sides and monitors a resultant waveform of the sensor cell current to determine the value of the pump cell-applied voltage when the value of the sensor cell current changes at the given rate.

17. A gas concentration measuring apparatus as set forth in claim 16, wherein said controller sweeps the voltage applied to the pump cell cyclically at different amplitudes and monitors the resultant waveform of the sensor cell current in each cycle to determine the value of the pump cell-applied voltage when the value of the sensor cell current changes at the given rate.

18. A gas concentration measuring apparatus as set forth in claim 16, wherein said controller sweeps the voltage being applied to the pump cell sequentially both to the higher and lower voltage sides and measures resulting changes in the sensor cell current, when the resulting changes are substantially identical with each other, said controller determining that the value of the pump cell-applied voltage when the value of the sensor cell current changes at the given rate remains unchanged.

19. A gas concentration measuring apparatus as set forth in claim 16, wherein said controller sweeps the value of the voltage being applied to the pump cell both to the higher and lower voltage sides sequentially to measure the resulting changes in the sensor cell current, respectively, when the changes are different from those appearing at an initial characteristic of said gas concentration sensor and from each other, said controller determining that the value of the pump cell-applied voltage when the value of the sensor cell current changes at the given rate has shifted in a direction opposite a direction in which a change in the voltage applied to the pump cell results in an increase in the sensor cell current.

20. A gas concentration measuring apparatus as set forth in claim 1, wherein said controller controls the voltage applied to the pump cell as a function of the pump cell current produced by the pump cell by look-up using a predetermined voltage-to-current relation and determines the concentration of the specified gas component in a gas concentration measuring cycle, and wherein said controller works to determine the control point and correct the voltage applied to the pump cell to the control point in a correction cycle which does not coincide with the gas concentration measuring cycle.

21. A gas concentration measuring apparatus as set forth in claim 1, further comprising a deterioration determining circuit which works to determine a degree of deterioration of said gas concentration sensor based on the value of the pump cell-applied voltage when the value of the sensor cell current changes at the given rate.

22. A gas concentration measuring apparatus as set forth in claim 1, wherein said controller looks up a predetermined voltage-to-current relation to determine the value of the voltage to be applied to the pump cell as a function of an instant value of the pump cell current produced by the pump cell, and wherein said controller defines a difference between a value of the pump cell-applied voltage on the control point and the value of the voltage applied to the pump cell determined using the voltage-to-current relation as a voltage correction value and stores the voltage correction value in a backup memory.

23. A gas concentration measuring apparatus as set forth in claim 1, wherein said controller looks up a predetermined voltage-to-current relation to determine the value of the voltage to be applied to the pump cell as a function of an instant value of the pump cell current produced by the pump cell, and wherein said controller corrects the voltage-to-current relation using a value of the pump cell-applied voltage on the control point.

24. A gas concentration measuring apparatus as set forth in claim 1, wherein the gasses admitted into the gas chamber are exhaust gasses of an automotive engine, and wherein said controller works to control the voltage to be applied to the pump cell at startup or rest of the engine.

* * * * *